US008314252B2

(12) United States Patent
Paquette et al.

(10) Patent No.: US 8,314,252 B2
(45) Date of Patent: Nov. 20, 2012

(54) PROCESS FOR PREPARING OXAZOLINE-PROTECTED AMINODIOL COMPOUNDS USEFUL AS INTERMEDIATES TO FLORFENICOL

(75) Inventors: Leo A. Paquette, Columbus, OH (US); James C. Towson, Flemington, NJ (US)

(73) Assignees: Intervet Inc., Summit, NJ (US); Intervet International B.V., Boxmeer (NL)

( * ) Notice: Subject to any disclaimer, the term of this patent is extended or adjusted under 35 U.S.C. 154(b) by 0 days.

(21) Appl. No.: 13/056,006

(22) PCT Filed: Jul. 28, 2009

(86) PCT No.: PCT/US2009/051893
§ 371 (c)(1), (2), (4) Date: Mar. 24, 2011

(87) PCT Pub. No.: WO2010/014566
PCT Pub. Date: Feb. 4, 2010

(65) Prior Publication Data
US 2011/0166359 A1   Jul. 7, 2011

Related U.S. Application Data

(60) Provisional application No. 61/084,900, filed on Jul. 30, 2008.

(51) Int. Cl.
C07D 263/08 (2006.01)
C07C 233/00 (2006.01)
(52) U.S. Cl. ........................ 548/239; 564/212
(58) Field of Classification Search ............. 548/239; 564/212
See application file for complete search history.

(56) References Cited

U.S. PATENT DOCUMENTS

| 2,671,748 A | 3/1954 | Crooks |
| 3,405,165 A | 10/1968 | Rebstock |
| 3,475,470 A | 10/1969 | Rebstock |
| 3,740,411 A | 6/1973 | Aklyama et al. |
| 3,950,360 A | 4/1976 | Aoki et al. |
| 3,984,564 A | 10/1976 | Aoki et al. |
| 4,199,569 A | 4/1980 | Chabala et al. |
| 4,235,892 A | 11/1980 | Nagabhushan |
| 4,310,519 A | 1/1982 | Albers-Schonberg et al. |
| 4,311,857 A | 1/1982 | Nagabhushan |
| 4,582,918 A | 4/1986 | Nagabhushan et al. |
| 4,743,700 A | 5/1988 | Giancarlo et al. |
| 4,820,695 A | 4/1989 | Debono et al. |
| 4,876,352 A | 10/1989 | Schumacher et al. |
| 4,916,154 A | 4/1990 | Asato et al. |
| 4,973,750 A | 11/1990 | Nagabhushan et al. |
| 5,082,863 A | 1/1992 | Apelian et al. |
| 5,089,480 A | 2/1992 | Gibson et al. |
| 5,105,009 A | 4/1992 | Jommi et al. |
| 5,227,494 A | 7/1993 | Schumacher et al. |
| 5,288,710 A | 2/1994 | Cvetovich |
| 5,332,835 A | 7/1994 | Jommi et al. |
| 5,352,832 A | 10/1994 | Wu et al. |
| 5,382,673 A | 1/1995 | Clark et al. |
| 5,399,717 A | 3/1995 | Cvetovich et al. |
| 5,567,844 A | 10/1996 | Jommi et al. |
| 5,663,361 A | 9/1997 | Towson et al. |
| 5,908,937 A | 6/1999 | Jommi et al. |
| 5,958,888 A | 9/1999 | Macy et al. |
| 5,965,603 A | 10/1999 | Johnson et al. |
| 6,054,434 A | 4/2000 | Kropp et al. |
| 6,136,838 A | 10/2000 | Chern et al. |
| 6,174,540 B1 | 1/2001 | Williams et al. |
| 6,239,112 B1 | 5/2001 | Macy et al. |
| 6,270,768 B1 | 8/2001 | O'Connell et al. |
| 6,271,255 B1 | 8/2001 | Leadlay et al. |
| 6,339,063 B1 | 1/2002 | Kropp et al. |
| 6,437,151 B2 | 8/2002 | Leadlay et al. |
| 6,472,371 B1 | 10/2002 | Dirlam et al. |
| 6,514,492 B1 | 2/2003 | Gao et al. |
| 6,514,945 B1 | 2/2003 | Boettner |
| 6,733,767 B2 | 5/2004 | Chern et al. |
| 6,790,867 B2 | 9/2004 | Kohan et al. |
| 6,825,327 B2 | 11/2004 | Sklavounos et al. |
| 7,041,670 B2 | 5/2006 | Boojamra et al. |
| 7,126,005 B2 | 10/2006 | Handa et al. |
| 7,153,842 B2 | 12/2006 | Hecker et al. |
| 7,361,689 B2 | 4/2008 | Shuster et al. |
| 7,572,777 B2 | 8/2009 | Hecker et al. |
| 7,713,950 B2 | 5/2010 | Shuster et al. |
| 7,786,329 B2 | 8/2010 | Towson |
| 2004/0242546 A1 | 12/2004 | Freehauf et al. |
| 2005/0075506 A1 | 4/2005 | Handa et al. |
| 2005/0182139 A1 | 8/2005 | Shuster et al. |

(Continued)

FOREIGN PATENT DOCUMENTS

CN   1507858   6/2004

(Continued)

OTHER PUBLICATIONS

Adickes et al, "Über die Anlagerung von Alkali-Alkoholaten an Säureester", Journal für praktische Chemie, vol. 2, pp. 305-327 (1932) [Translation Attached]. Banerjee et al, "Photoreleasable Protecting Groups Based on Electron Transfer Chemistry. Donor Sensitized Release of Phenacyl Groups from Alcohols, Phosphates and Diacids", Tetrahedron, vol. 55, pp. 12699-12710 (1999).
Brunelle, "Novel Chatalysis of o-Nitrophenyl Carbonates by p-Dimethylaminopyridine", Tetrahedron Letters, vol. 23, No. 17, pp. 1739-1742 (1982).
Castro et al, "Kinetic Investigation of the Phenolysis of Phenyl 4-Nitrophenyl and Phenyl 2,4-Dinitrophenyl Carbonates", J. Chem. Soc. Perkin Trans., vol. 2, pp. 2351-2354 (2001).
Chen et al, "Synthesis of (+)-CP-263,114", J. Am. Chem. Soc., vol. 122, pp. 7424-7425 (2000).

(Continued)

*Primary Examiner* — Joseph K McKane
*Assistant Examiner* — Samantha Shterengarts
(74) *Attorney, Agent, or Firm* — David J. Kerwick

(57) ABSTRACT

Processes for preparing oxazoline compounds are disclosed. These oxazoline compounds are useful intermediates in the preparation of Florfenicol and related compounds.

6 Claims, No Drawings

U.S. PATENT DOCUMENTS

| | | | |
|---|---|---|---|
| 2007/0055066 | A1 | 3/2007 | Towson |
| 2007/0055067 | A1 | 3/2007 | Towson |
| 2007/0055080 | A1 | 3/2007 | Towson |
| 2007/0155799 | A1 | 7/2007 | Glinka et al. |
| 2008/0145317 | A1 | 6/2008 | Tongiani et al. |
| 2008/0146640 | A1 | 6/2008 | Glinka |
| 2008/0153906 | A1 | 6/2008 | Celly et al. |
| 2008/0188556 | A1 | 8/2008 | Glinka |
| 2008/0319200 | A1 | 12/2008 | Towson |
| 2009/0062397 | A1 | 3/2009 | Tongiani |
| 2009/0149657 | A1 | 6/2009 | Gnidovec et al. |
| 2009/0156683 | A1 | 6/2009 | Simmons et al. |
| 2009/0170954 | A1 | 7/2009 | Towson et al. |
| 2009/0275662 | A1 | 11/2009 | Barbot |
| 2010/0210851 | A1 | 8/2010 | Towson |
| 2011/0166359 | A1 | 7/2011 | Paquette et al. |

FOREIGN PATENT DOCUMENTS

| | | |
|---|---|---|
| DE | 117095 | 1/1901 |
| DE | 830956 | 2/1952 |
| EP | 0 674 618 | 9/1998 |
| EP | 0 500 177 | 1/1999 |
| EP | 0 980 248 | 10/2001 |
| EP | 0 922 040 | 12/2004 |
| GB | 698543 | 10/1953 |
| GB | 804986 | 11/1958 |
| GB | 1173562 | 12/1969 |
| GB | 1263116 | 2/1972 |
| WO | 92/04016 | 3/1992 |
| WO | 92/07824 | 5/1992 |
| WO | 94/14764 | 7/1994 |
| WO | 98/06700 | 2/1998 |
| WO | 98/07709 | 2/1998 |
| WO | 02/41899 | 5/2002 |
| WO | 03/077828 | 9/2003 |
| WO | 03/097054 | 11/2003 |
| WO | WO03093221 * | 11/2003 |
| WO | 2004/089355 | 10/2004 |
| WO | 2006/136919 | 12/2006 |
| WO | 2007/030385 | 3/2007 |
| WO | 2007/030386 | 3/2007 |
| WO | 2007/030405 | 3/2007 |
| WO | 2008/150406 | 12/2008 |
| WO | 2009/015111 | 1/2009 |
| WO | 2010/014566 | 2/2010 |

OTHER PUBLICATIONS

Chmielewski et al, "Thermolytic Carbonates for Potential 5'-Hydroxyl Protection of Deoxyribonucleosides", J. Org. Chem., vol. 68, pp. 10003-10012 (2003).

Couture et al, "A New Synthetic Route to the Previously Unattainable 2-Arylpyrido[2,3-b][1,5]thiazepin-4(5H)-ones", Journal of Organic Chemistry, vol. 55, No. 14, pp. 4337-4339 (1990).

Diaz et al, CAL-B-Catalyzed Alkoxycarbonylation of A-Ring Stereoisomeric Synthons of 1α,25-Dihydroxyvitamin D3: A Comparative Study. First Regioselective Chemoenzymatic Synthesis of 19-nor-A-Ring Carbonates, J. Org.Chem., vol. 66, pp. 4227-4232 (2001).

Dubowchik et al, "Cathepsin B-Sensitive Dipeptide Prodrugs. 2. Models of Anticancer Drugs Paclitaxel (Taxol®), Mitomycin C and Doxorubicin", Bioorganic & Medicinal Chemistry Letters, vol. 8, pp. 3347-3352 (1998).

Evers et al., "Synthese and spektroskopische Eigenschaften chiraler 1,2-Oxazolidine", Journal Fur Praktische Chemie., vol. 333, pp. 699-710, (1991).

Greiner et al, "Synthesis of Phosphoramidite Building Blocks of 2'-Amino-2'deoxyribonucleosides: New Compounds for Oligonucleotide Synthesis", Helvetica Chimica Acta, vol. 81, pp. 1528-1544 (1998).

Harada et al, "Allyloxycarbonyl Group as a Protective Group for the Hydroxyl Group in Carbohydrates", J. Carbohydrate Chemistry, vol. 14, No. 1, pp. 165-170 (1995).

Iimori et al, "A Novel Intramolecular Decarboxylative Glycosylation via Mixed Carbonate", Tetrahedron Letters, vol. 37, No. 13, pp. 2267-2270 (1996).

Kenar et al, "Synthesis and Characterization of Dialkyl Carbonates Prepared from Mid-, Long-Chain, and Guerbet Alcohols", J. Am. Oil Chem. Soc., vol. 81, No. 3, pp. 285-291 (2004).

Kozikowski et al, "Novel PI Analogues Selectively Block Activation of the Pro-Survival Serine/Threonine Kinase Akt", J. Am. Chem. Soc., vol. 125, pp. 1144-1145 (2003).

Kryczka et al, "Syntheses de Carbonates et Carbamates Benzyliques et Allyliques", Bull. Soc. Chim. Belg., FR, vol. 101, No. 2, pp. 147-157 (1992) [Abstract].

Li et al., "Synthesis of DNA Oligomers Possessing a Covalently Cross-Linked Watson—Crick Base Pair Model", Angew. Chem., vol. 113, No. 8, pp. 1519-1523 (2001).

Marca et al, "Observations on Antibacterial Activity of Thiamphenicol Glycinate Acetylcysteinate", Quademi Sclavo di Diagnostica Clinica e di Laboratorio, vol. 15, No. Suppl. 1, pp. 777-784 (Jun. 1979) [Abstract].

Mindl et al, "Alkoxycarbonylation of Alcohols and phenols by Nitrosoformates", Collect. Czech. Chem. Commun., vol. 61, pp. 1053-1063 (1996).

Moris et al, "A Novel and Convenient Route to 3'-Carbonates from Unprotected 2'-Deoxynucleosides Through an Enzymatic Reaction", J. Org. Chem., vol. 57, pp. 2490-2492 (1992).

Moris et al, "Enzymatic Acylation and Alkoxycarbonylation of α-, Xylo-, Anhydro-, and Arabino-Nucleosides", Tetrahedron, vol. 49, No. 44, pp. 10089-10098 (1993).

Müller et al, "Carbenoid Pathways in Copper-Catalyzed Intramolecular Cyclopropanations of Phenyliodonium Ylides", Helvetica Chimica Acta, vol. 84, No. 5, pp. 1093-1111 (2001).

Nongkunsarn et al, Rearrangement and Radical Mediated Decarboxylation of Trimethylsilyl Benzoates Using Xenon Difluoride, J. Chem. Soc. Perkin Trans., vol. 1, No. 2, pp. 121-122 (1996) [Abstract].

Olofson et al, "A Regiospecific and Stereospecific Route to Enol Carbonates and Carbamates: Closer Look at a 'Naked Anion'", Tetrahedron Letters, vol. 21, pp. 819-822 (1980).

Peri et al, "Preparation of Bicyclo[3.2.0]heptane-2-endo,7-endo-diols:1,3-Diols with a Chiral Riged Backbone", J. Org. Chem., vol. 69, pp. 1353-1356 (2004).

Pulido et al, "Enzymatic Regioselective Alkoxycarbonylation of Hexoses and Pentoses with Carbonate Oxime Esters", J. Chem. Soc. Perkin Trans., vol. 1, pp. 589-592 (1993).

Rege et al, "Chemoenzymatic Synthesis and High-Throughput Screening of an Aminoglycoside—Polyamine Library: Identification of High-Affinity Displacers and DNA-Binding Ligands", J. Am. Chem.Soc., vol. 126, pp. 12306-12315 (2004).

Schirmeister et al, "The 2-(4-Nitrophenyl)ethoxycarbonyl (npeoc) and 2-(2,4-Dinitrophenyl)ethoxycarbonyl (dnpeoc) Groups for Protection of Hydroxy Functions in Ribonucleosides and 2'-Deoxyribonucleosides", Helvetica Chimica Acta, vol. 76, pp. 385-401 (1993).

Shue et al, "Novel Methodology for the Synthesis of trans-Alkene Dipeptide Isosteres", J. Org. Chem., vol. 56, pp. 2107-2111 (1991).

Schumacher et al, "An Efficient Synthesis of Florfenicol", Journal of Organic Chemistry, American Chemical Society, vol. 55, No. 18, pp. 5291-5294 (1990).

Seitz et al, "Modular Synthesis of Chiral Pentadentate Bis(Oxazoline) Ligands", Tetrahedron, vol. 62, No. 42, pp. 9973-9980 (2006).

Takamizawa et al, "Studies of the Pyrimidine Derivatives. XXV. The Reaction of Alkoxycarbonylthiocyanates and Related Compounds with the Sodium Salt of Thiamine", Bull. Chem. Soc. Jpn., vol. 36, No. 9, pp. 1214-1220 (1963).

Von Dem Bruch et al, "The 3-(3-Pyridyl)allyloxycarbonyl (Paloc) Moiety—a Stable, Amino Protecting Group for Peptide Syntheses in Organic Media and in Water That is Cleavable under Neutral Conditions", Angew. Chem., vol. 102, No. 12, pp. 1520-1522 (1990).

Wang et al, "Solid Phase Synthesis of Neutral Oligonucleotide Analogues", Tetrahedron Letters, vol. 32, No. 50, pp. 7385-7388 (1991).

Weber et al, "Steryl and Stanyl Esters of Fatty Acids by Solvent-Free Esterification and Transesterification in Vacuo Using Lipases from *Rhizomucor miehei, Candida antarctica*, and *Carica papaya*", J. Agric. Food Chem., vol. 49, pp. 5210-5216 (2001).

Whalen et al, "Resolution of a Chiral Alcohol Through Lipase-Catalyzed Transesterification of its Mixed Carbonate by poly(ethylene glycol) in Organic Media", Tetrahedron: Asymmetry, vol. 11, pp. 1279-1288 (2000).

Williams et al, "Samarium Barbier Reactions of α-Iodomethyloxazoles and Thiazoles with Aliphatic Aldehydes", Organic Letters, vol. 7, No. 19, pp. 4099-4102 (2005).

Wu et al, "An Improved Industrial Synthesis of Florfenicol Plus and Enantioselective Total Synthesis of Thiamphenicol and Florfenicol", Journal of Organic Chemistry, American Chemical Society, vol. 62, No. 9, pp. 2996-2998 (1997).

Wuts et al, "New Process for the Preparation of Methyl Carbonates", Organic Letters, vol. 5, No. 9, pp. 1483-1486 (2003).

Yadav et al, "A Remarkably Efficient markovnikov Hydrochlorination of Olefins and Transformation of Nitriles into Imidates by Use of AcCl and an Alcohol", European J. Org. Chem., vol. 2, pp. 452-456 (2005).

Freedom of Information Summary, Original New Animal Drug Application, NADA 141-265 Sponsored by Schering-Plough Animal Health, Approved Mar. 21, 2008.

Nuflor Package Insert.

Veterinary Pharmaceuticals and Biologicals, The Veterinarian's PDR, Veterinary Medicien Publishing Group, pp. 652 (1997-1998).

International Search Report for corresponding PCT/US2009/051893, mailed Mar. 4, 2010.

International Search Report for corresponding PCT/US2007/025319, mailed May 29, 2008.

* cited by examiner

PROCESS FOR PREPARING OXAZOLINE-PROTECTED AMINODIOL COMPOUNDS USEFUL AS INTERMEDIATES TO FLORFENICOL

Related Applications

This application is a national stage entry under 35 U.S.C. §371 of PCT/US2009/051893filed on July 28, 2009, which claims priority to U.S. Provisional Application No. 61/084,900 filed on July 30, 2008.

TECHNICAL FIELD

The present invention relates generally to new processes for preparing oxazoline compounds by reaction of an imidate or its acid addition salt with a 2-amino-1,3-propanediol compound or a 2-amino-3-hydroxy propanoate compound. The resulting oxazoline compounds are useful intermediates in the preparation of Florfenicol and related compounds.

BACKGROUND OF THE INVENTION

Florfenicol, also known as 2,2-dichloro-N-[(1S,2R)-1-(fluoromethyl)-2-hydroxy-2-[4-(methylsulfonyl)phenyl]ethyl}-acetamide or [R—(R*,S*)]-2,2-Dichloro-N-[1-(fluoromethyl)-2-hydroxy-2-[4-(methylsulfonyl)phenyl]ethyl] acetamide, is a broad spectrum antibiotic of Formula I. Florfenicol is a structural analog of thiamphenicol, which in turn is a derivative of chloramphenicol [see, e.g., U.S. Pat. No. 4,235,892, U.S. Pat. No. 5,352,832, the contents of which are hereby incorporated by reference in their entireties].

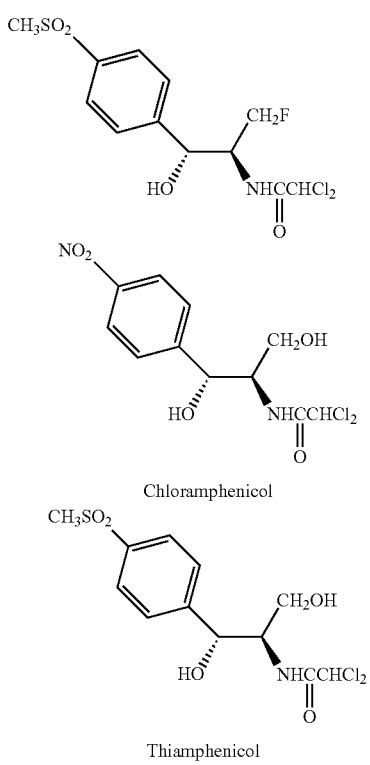

Florfenicol has broad spectrum antibiotic activity against many gram-negative and gram-positive bacteria, including utility in the prevention and treatment of bacterial infections due to susceptible pathogens in birds, reptiles, fish, shellfish and mammals. One of florfenicol's primary uses is in the treatment of pneumonia and associated respiratory infections in cattle (often referred to generically as Bovine Respiratory Disease or BRD) caused by *Mannhemia haemolytica, Pasturella multocida* and/or *Haemophilus somnus*, also known as *Histophilus somni*. It is also indicated in the treatment of: pododermatitis in cattle caused by *Fusobacterium necrophorum* and *Bacterioides melaminogenicus*; swine respiratory disease caused by *Pasteurella multocida, Actinobacillus pleuropneumoniae, Streptococcus suis, Salmonella cholerasuis* and/or *Mycoplasma* spp.; colibacillosis in chickens caused by *Escherichia coli*; enteric septicemia in catfish caused by *Edwardsiella ictaluri*; and furunculosis in salmon caused by *Aeromonas salmonicida*. Other genera of bacteria that have exhibited susceptibility to florfenicol include *Enterobacter, Klebsiella, Staphylococcus, Enterococcus, Bordetella, Proteus* and *Shigella*. In particular, chloramphenicol-resistant strains of organisms, such as *K. pneumoniae, E. cloacae, S. typhus* and *E. coli*, are susceptible to florfenicol.

Florfenicol is used in veterinary medicine where the cost of goods is a major factor for the consumer. It is therefore important to have chemically efficient and economical processes for its manufacture. Such processes assure that this important antibiotic is available to the consumer at a competitive price.

The citation of any reference herein should not be construed as an admission that such reference is available as "Prior Art" to the instant application.

SUMMARY OF THE INVENTION

In some embodiments, the present invention provides a process for preparing an ester oxazoline compound of Formula III:

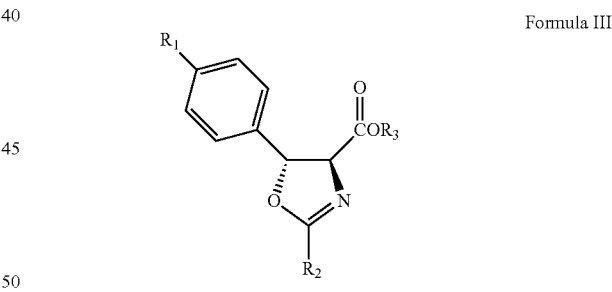

wherein:

$R_1$ is hydrogen, methylthio, methylsulfoxy, methylsulfonyl, fluoromethylthio, fluoromethylsulfoxy, fluoromethylsulfonyl, nitro, fluoro, bromo, chloro, acetyl, benzyl, phenyl, halo substituted phenyl, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{3-6}$ heterocyclic group;

$R_2$ is hydrogen, $C_{1-6}$ alkyl, $C_{1-6}$ haloalkyl, $C_{1-6}$ dihaloalkyl, $C_{1-6}$ trihaloalkyl, $CH_2Cl$, $CHCl_2$, $CCl_3$, $CH_2Br$, $CHBr_2$, $CBr_3$, $CH_2F$, $CHF_2$, $CF_3$, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, $C_{1-6}$ alkyl or $C_{1-6}$ alkoxy; $C_{1-6}$ alkylcarboxy, $C_{1-6}$ haloalkylcarboxy, $C_{3-8}$ cycloalkylcarboxy, $C_{2-6}$ alkenylcarboxy, $C_{2-6}$ alkenylcarboxy, $C_{2-6}$ alkynylcarboxy, $C_{1-6}$ alkoxycarboxy, $C_{3-6}$ heterocyclic carboxy, benzylcarboxy, phenylcarboxy, phenyl alkylcarboxy where the phenyl ring may be substituted by one or two halogens, $C_{1-6}$ alkyl or $C_{1-6}$ alkoxy or an acid addition salt thereof; and $R_3$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy.

The ester oxazoline of Formula III can be prepared by a method including the step of:

reacting an imidate of Formula IV or an acid addition salt thereof:

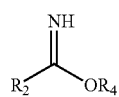

Formula IV wherein:

$R_2$ is as previously defined and $R_4$ is hydrogen, $C_{1-6}$ alkyl, $C_{1-6}$haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{3-6}$ heterocyclic group, benzyl, phenyl or phenyl alkyl where the phenyl ring may be substituted by one or two halogens, $C_{1-6}$ alkyl or $C_{1-6}$ alkoxy or an acid addition salt thereof, with a 2-amino-3-hydroxy propanoate compound of Formula VI:

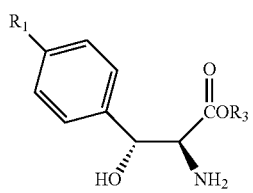

Formula VI wherein $R_1$ and $R_3$ are as previously defined, in the presence of a solvent to form an ester oxazoline of Formula III. Optionally, an acid or base may be employed to facilitate the reaction of the compound of Formula IV or its acid addition salt with the compound of Formula VI to form the ester oxazoline compound of Formula III.

In particular embodiments, the solvent employed for forming a compound of Formula III is selected from the group consisting of acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

A wide range of acids or bases can optionally be employed to facilitate the reaction of the compound of Formula IV or its acid addition salt with the compound of Formula VI to form the ester oxazoline compound of Formula III.

A non-limiting list of suitable acids includes inorganic acids, such as dilute aqueous hydrochloric acid, sulfuric acid, nitric acid, phosphoric acid and a mixture thereof, as well as organic acids, such as acetic acid, trifluoroacetic acid, methanesulfonic acid, p-toluene sulfonic acid and a mixture thereof. In some embodiments, the acid catalyst is a mixture of at least one inorganic acid and at least one organic acid. In some embodiments, the acid catalyst comprises p-toluene sulfonic acid.

A non-limiting list of suitable bases includes inorganic bases, such as LiOH, NaOH, KOH, $Li_2CO_3$, $Na_2CO_3$, $K_2CO_3$, $NH_4OH$ and a mixture thereof, as well as organic bases such as triethylamine, trimethylamine, pyridine and a mixture thereof. In some embodiments, the base is a mixture of at least one inorganic base and at least one organic base. In some embodiments, the base comprises triethylamine.

In some embodiments, the present invention provides a process for preparing an oxazoline compound of Formula II:

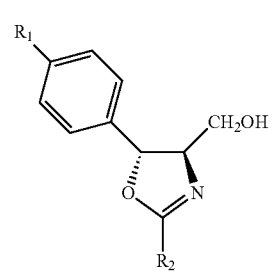

Formula II wherein $R_1$ and $R_2$ are as previously defined.

The oxazoline of Formula II can be prepared by a method including the steps of:

a) reducing a compound of Formula VI:

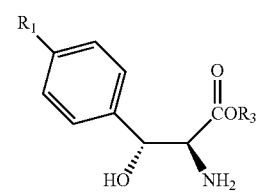

Formula VI wherein:

$R_1$ and $R_3$ are as previously defined, (with or without isolation) in the presence of a solvent to form a compound of Formula V:

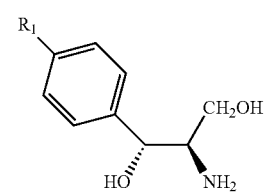

Formula V wherein $R_1$ is as previously defined, b) reacting an imidate or an acid addition salt thereof of Formula IV:

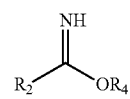

Formula IV wherein:

R$_2$ and R$_4$ are as previously defined, in a solvent with a compound of Formula V resulting from step a) to form a compound of Formula II. Optionally, an acid or base may be employed to facilitate the reaction of the compound of Formula IV or its acid addition salt with the compound of Formula V to form the ester oxazoline compound of Formula II.

In particular embodiments, the reduction is carried out with a reducing agent which comprises NaBH$_4$, KBH$_4$, Ca(BH$_4$)$_2$, LiBH$_4$, or a mixture thereof.

In particular embodiments, the solvent employed during reduction is selected from the group consisting of water, methanol, ethanol, propanol, isopropanol, butanol, pentanol, and mixtures thereof.

In particular embodiments, the imidate of Formula IV or its acid addition salt reacts in a solvent selected from acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

A wide range of acids or bases can optionally be employed to facilitate the reaction of the compound of Formula IV or its acid addition salt with the compound of Formula V to form the compound of Formula II.

A non-limiting list of suitable acids includes inorganic acids, such as dilute aqueous hydrochloric acid, sulfuric acid, nitric acid, phosphoric acid and a mixture thereof, as well as organic acids, such as acetic acid, trifluoroacetic acid, methanesulfonic acid, p-toluene sulfonic acid and a mixture thereof. In some embodiments, the acid catalyst is a mixture of at least one inorganic acid and at least one organic acid. In some embodiments, the acid catalyst comprises p-toluene sulfonic acid.

A non-limiting list of suitable bases includes inorganic bases, such as LiOH, NaOH, KOH, Li$_2$CO$_3$, Na$_2$CO$_3$, K$_2$CO$_3$, NH$_4$OH and a mixture thereof, as well as organic bases such as triethylamine, trimethylamine, pyridine and a mixture thereof. In some embodiments, the base is a mixture of at least one inorganic base and at least one organic base. In some embodiments, the base comprises triethylamine.

In some embodiments of the invention, a compound of Formula III is reduced (with or without isolation) in the presence of a solvent to form a compound of Formula II.

In particular embodiments, the reduction of Formula III to Formula II is carried out with a reducing agent which comprises NaBH$_4$, KBH$_4$, Ca(BH$_4$)$_2$, LiBH$_4$, or a mixture thereof.

In particular embodiments, the solvent employed during reduction of Formula III to Formula II is selected from the group consisting of water, methanol, ethanol, propanol, isopropanol, butanol, pentanol, and mixtures thereof.

In some embodiments, processes of the invention continue by fluorinating a compound of Formula II (with or without isolation) in the presence of a solvent to form a compound of Formula VII:

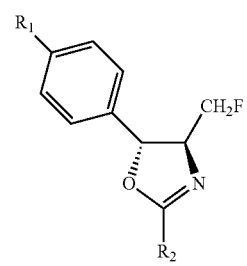

Formula VII wherein R$_1$ and R$_2$ are as previously defined.

In particular embodiments, the fluorination is carried out with a fluorinating agent comprising sodium fluoride, potassium fluoride, cesium fluoride, tetrabutylammonium fluoride, 1,1,2,2,3,3,4,4,4-nonafluoro-1-butanesulfonyl fluoride, chloromethyl-4-fluoro-1,4-diazoniabicyclo[2.2.2]octane bis-(tetrafluoroborate), N-(2-chloro-1,1,2-trifluoroethyl)diethylamine, N-(2-chloro-1,1,2-trifluoroethyl)dimethylamine, N-(2-chloro-1,1,2-trifluoroethyl)dipropylamine, N-(2-chloro-1,1,2-trifluoroethyl)pyrrolidine, N-(2-chloro-1,1,2-trifluoroethyl)-2-methylpyrrolidine, N-(2-chloro-1,1,2-trifluoroethyl)-4-methylpiperazine, N-(2-chloro-1,1,2-trifluoroethyl)-morpholine, N-(2-chloro-1,1,2-trifluoroethyl)piperidine, 1,1,2,2-tetrafluoroethyl-N,N-dimethylamine, (Diethylamino)sulfur trifluoride, Bis-(2-methoxyethyl)aminosulfur trifluoride, N,N-diethyl-1,1,2,3,3,3-hexafluoro-1-propanamine, or a mixture thereof.

In particular embodiments, the fluorinating agent is N,N-diethyl-1,1,2,3,3,3-hexafluoro-1-propanamine (Ishikawa reagent).

In particular embodiments, the solvent employed during fluorination is selected from the group consisting of 1,2-dichloroethane, methylene chloride, chloroform, carbon tetrachloride, chlorobenzene, a chlorinated hydrocarbon, and mixtures thereof.

In some embodiments, processes of the invention continue by hydrolyzing a compound of Formula VII (with or without isolation) to form a compound of Formula VIII:

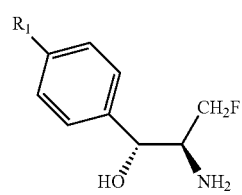

Formula VIII wherein R$_1$ is as defined above.

In particular embodiments, the hydrolysis is carried out with an acidic or basic catalyst in a solvent. A wide range of suitable acidic and basic catalysts can be employed without limitation. In some embodiments, the acidic catalyst includes HCl, HNO$_3$, H$_2$SO$_4$, H$_3$PO$_4$, acetic acid, trifluoroacetic acid, methanesulfonic acid, an organic acid of the Formula R$_4$C(O)OH wherein R$_4$ is as defined above, or mixtures thereof. In particular embodiments, the acidic catalyst is HCl. In some embodiments, the basic catalyst includes NaOH, KOH, LiOH, Na$_2$CO$_3$, K$_2$CO$_3$, NaHCO$_3$, KHCO$_3$, NH$_4$OH, triethylamine, trimethylamine, sodium methoxide, sodium ethoxide, potassium methoxide, potassium ethoxide, or mixtures thereof. In particular embodiments, the basic catalyst includes NaOH, KOH, NH$_4$OH, or a mixture thereof.

In particular embodiments, the solvent is selected from the group consisting of acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water and mixtures thereof.

Processes of the invention continue in some embodiments by acylating a compound of Formula VIII (with or without isolation) in the presence of a solvent and a base by a compound of the Formula $R_5COR_2$, wherein $R_2$ is a previously defined and $R_5$ is OH, $C_{1-6}$ alkoxy or halo, to produce a compound of Formula IX:

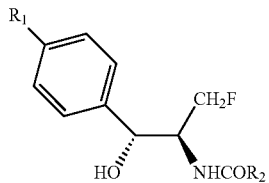

Formula IX wherein $R_1$ and $R_2$ are as previously defined.

In particular embodiments, the acylation is carried out with an acylating agent comprising dichloroacetic acid or a reactive derivative thereof.

In particular embodiments, the acylation is carried out with methyl dichloroacetate, ethyl dichloroacetate, dichloroacetylchloride, or a mixture thereof. In particular embodiments, the acylation is carried out with methyl dichloroacetate.

In particular embodiments, the solvent employed during acylation is selected from the group consisting of acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

In particular embodiments, the base includes an organic base, an inorganic base and mixtures thereof.

In some embodiments, processes of the invention continue by selectively hydrolyzing a compound of Formula VII (with or without isolation) to form a compound of Formula IX.

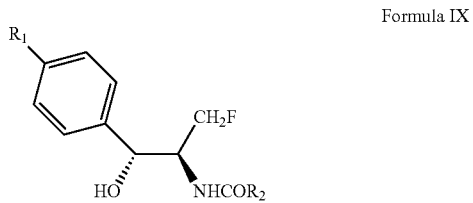

Formula IX wherein $R_1$ and $R_2$ are as defined above.

In particular embodiments, the selective hydrolysis is carried out with water and an acidic catalyst or basic catalyst in a solvent.

A wide range of acid catalysts can be employed in carrying out a process of the present invention. A non-limiting list of suitable acid catalysts includes inorganic acids, such as dilute aqueous hydrochloric acid, sulfuric acid, nitric acid, phosphoric acid and a mixture thereof, as well as organic acids, such as acetic acid, trifluoroacetic acid, methanesulfonic acid, p-toluene sulfonic acid and a mixture thereof. In some embodiments, the acid catalyst is a mixture of at least one inorganic acid and at least one organic acid. In some embodiments, the acid catalyst comprises p-toluene sulfonic acid.

A wide range of basic catalysts can be employed in carrying out of a process of the present invention. A non-limiting list of suitable basic catalysts includes inorganic bases, such as LiOH, NaOH, KOH, $Li_2CO_3$, $Na_2CO_3$, $K_2CO_3$, $NH_4OH$ and a mixture thereof, as well as organic bases such as sodium methoxide, sodium ethoxide, potassium methoxide, potassium ethoxide and a mixture thereof. In some embodiments, the basic catalyst is a mixture of at least one inorganic acid and at least one organic acid. In some embodiments, the basic catalyst comprises $NH_4OH$.

In some embodiments of the invention, the temperature during formation of a compound of Formula IX by selective hydrolysis is less than or equal to about 100° C. In particular embodiments, the temperature is less than about 30° C.

In particular embodiments, the solvent is selected from acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

In some embodiments, the organic solvent comprises isopropanol, methylene chloride or a mixture thereof. In some embodiments, the mixture of an organic solvent and water comprises methylene chloride and water. In some embodiments, about 0.5 to about 3 molar equivalents of water are used for each mole of the compound of Formula VII. In some embodiments, about 1 to about 2 molar equivalents of water are used for each mole of the compound of Formula VII.

In particular embodiments, the present invention provides a process for preparing florfenicol by a method including the steps of:

reacting

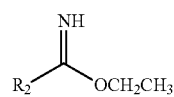

or its acid additional salt, wherein $R_2$ is $CHCl_2$ or phenyl, with

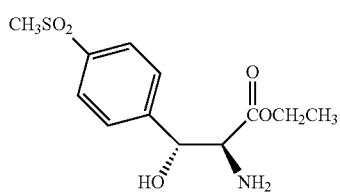

in the presence of a solvent to form

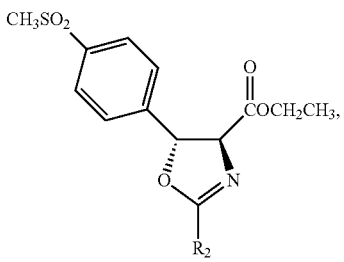

reducing the resulting product (with or without isolation) in the presence of a solvent to form

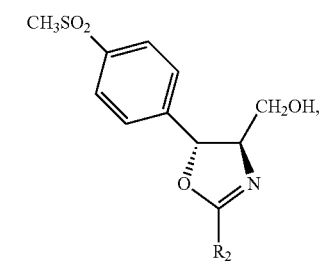

fluorinating the resulting product (with or without isolation) in the presence of a solvent to form

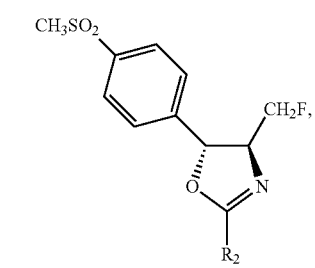

hydrolyzing the resulting product (with or without isolation) to form

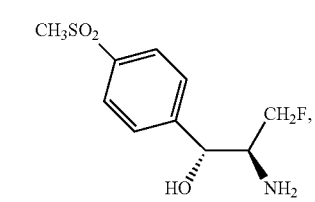

acylating the resulting product (with or without isolation) in the presence of a solvent and a base by a compound of the Formula CHCl$_2$COOCH$_3$ to form

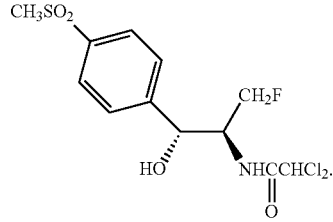

In particular embodiments, R$_2$ is phenyl.

In particular embodiments, the present invention provides a process for preparing florfenicol by a method including the steps of:

reacting

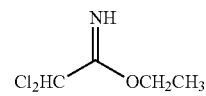

or its acid additional salt, with

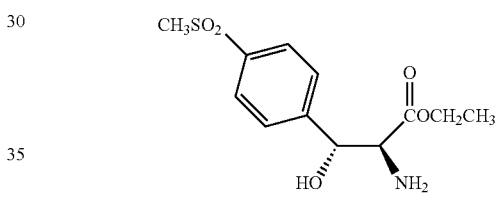

in the presence of a solvent to form

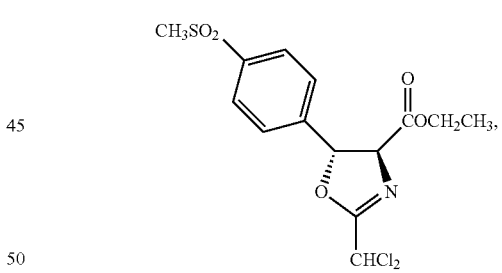

reducing the resulting product (with or without isolation) in the presence of a solvent to form

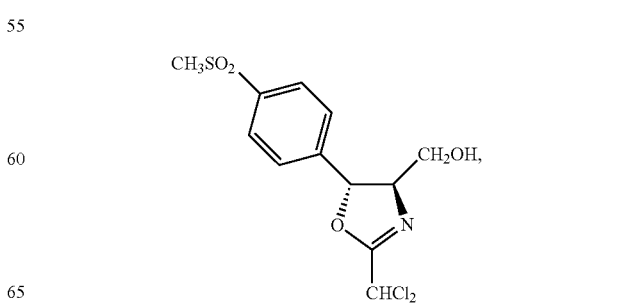

fluorinating the resulting product (with or without isolation) in the presence of a solvent to form

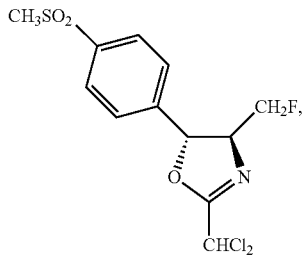

selectively hydrolyzing the resulting product (with or without isolation) to form

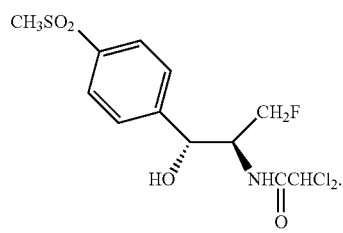

In particular embodiments, the present invention provides a process for preparing florfenicol by a method including the steps of:
reducing

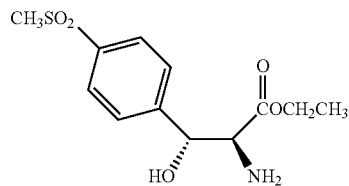

(with or without isolation) in the presence of a solvent to form

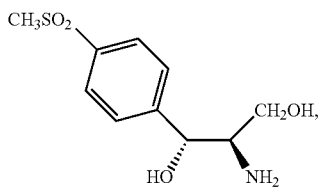

reacting the resulting product with

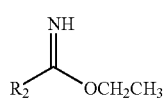

or its acid additional salt, wherein $R_2$ is $CHCl_2$ or phenyl, to form

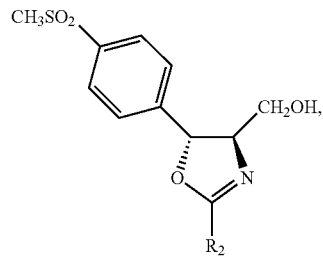

fluorinating the resulting product (with or without isolation) in the presence of a solvent to form

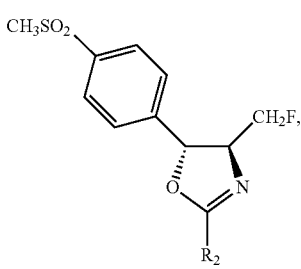

hydrolyzing the resulting product (with or without isolation) to form

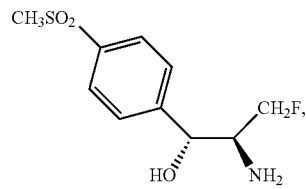

acylating the resulting product (with or without isolation) in the presence of a solvent and a base by a compound of the Formula $CHCl_2COOCH_3$ to form

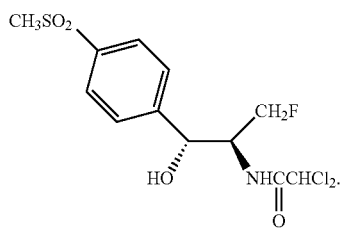

In particular embodiments, $R_2$ is phenyl.
In particular embodiments, the present invention provides a process for preparing florfenicol by a method including the steps of:
reducing

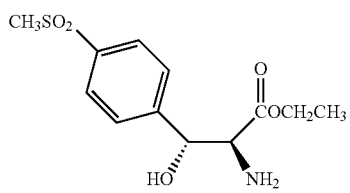

(with or without isolation) in the presence of a solvent to form

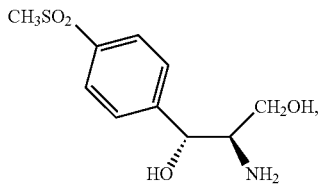

reacting the resulting product with

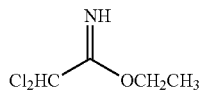

or its acid additional salt, to form

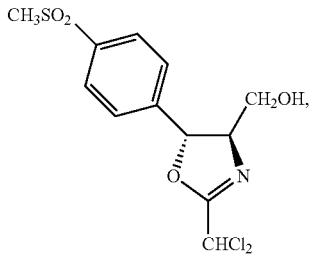

fluorinating the resulting product (with or without isolation) in the presence of a solvent to form

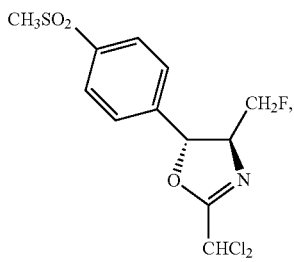

selectively hydrolyzing the resulting product (with or without isolation) to form

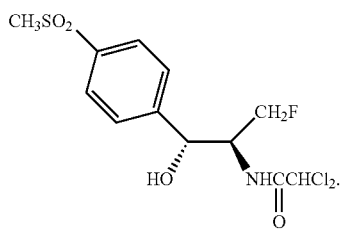

In some embodiments, processes of the invention continue by purifying a compound of Formula IX with a mixture comprising a $C_{1-10}$ alkyl mono, di or tri alcohol and water to form a pure form of a compound of Formula IX. In some embodiments of the invention, a compound of Formula IX is Florfenicol when $R_1$ is methyl sulfonyl and $R_2$ is $CHCl_2$.

The process of the invention provides economical alternatives and practical routes to the compounds of Formulas II and III. These compounds are useful intermediates in the preparation of Florfenicol.

DETAILED DESCRIPTION OF THE INVENTION

When used herein and in the appended claims, the terms listed below, unless otherwise indicated, will be used and are intended to be defined as indicated immediately below. Definitions for other terms can occur throughout the specification. It is intended that all terms used include the plural, active tense and past tense forms of a term.

The term "acetyl" means a $CH_3CO$— radical.

The term "alcoholic solvent" includes $C_1$ to $C_{10}$ monoalcohols such as methanol, ethanol, and mixtures thereof, $C_2$ to $C_{10}$ dialcohols such as ethylene glycol and $C_1$ to $C_{10}$ trialcohols such as glycerin. Alternatively, the term alcoholic solvent includes such alcohol admixed with any suitable cosolvent (i.e., a second solvent added to the original solvent, generally in small concentrations, to form a mixture that has greatly enhanced solvent powers due to synergism). Such cosolvents can include other solvents which are miscible with the alcoholic solvent such as $C_4$ to $C_{10}$ alkanes, aromatic solvents such as benzene, toluene, and xylenes, halobenzenes such as chlorobenzene, and ethers such as diethylether, tert-butylmethylether, isopropylether and tetrahydrofuran, or mixtures of any of the above cosolvents.

The term "alkyl" means a saturated straight or branched alkyl such as methyl, ethyl, propyl, or sec-butyl. Alternatively, the number of carbons in an alkyl can be specified. For example, "$C_{1-6}$ alkyl" means an "alkyl" as described above containing 1, 2, 3, 4, 5 or 6 carbon atoms.

The term "$C_{2-6}$ alkenyl" means an unsaturated branched or unbranched hydrocarbon group having at least one double carbon-carbon (—C=C—) bond and containing 2, 3, 4, 5, or 6 carbon atoms. Example alkenyl groups include, without limitation, ethenyl, 1-propenyl, isopropenyl, 2-butenyl, 1,3-butadienyl, 3-pentenyl and 2-hexenyl, and the like.

The term "$C_{2-6}$ alkynyl" means an unsaturated branched or unbranched hydrocarbon group having at least one triple carbon-carbon (—C≡C—) bond and containing 2, 3, 4, 5, or 6 carbon atoms. Example alkynyl groups include, without limitation, ethynyl, 1-propynyl, 2-propynyl, 2-butynyl, 3-butynyl, 2-penten-4-nyl, and the like.

The term "$C_{1-6}$ alkoxy" means an alkyl-O— group, where the term "alkyl" is defined herein. Example alkoxy groups include, without limitation, methoxy, ethoxy, propoxy (e.g., n-propoxy and isopropoxy), t-butoxy, and the like.

The term "aryl" means phenyl, or phenyl substituted by $C_1$ to $C_6$ alkyl or "halo", where phenyl and halo are as defined herein.

The term "$C_{1-6}$ aralkyl" means a $C_{1-6}$ alkyl as defined herein substituted by an aryl group that is any radical derived from an aromatic hydrocarbon by the removal of a hydrogen atom.

The term "$C_{2-6}$ aralkenyl" means a $C_{2-6}$ alkenyl as defined herein substituted by an aryl group that is any radical derived from an aromatic hydrocarbon by the removal of a hydrogen atom.

The term "bromo" means the chemical element bromine

"Substituted benzyl" means benzyl substituted by $C_1$ to $C_6$ alkyl or "halo", where benzyl is the univalent radical $C_6H_5CH_2$, formally derived from toluene (i.e., methylbenzene).

The term "chloro" means the chemical element chorine.

The term "$C_{3-8}$ cycloalkyl" means a saturated cyclic hydrocarbon group (i.e., a cyclized alkyl group) containing 3, 4, 5, 6, 7 or 8 carbon atoms. Example cycloalkyl groups include, without limitation, cyclopropyl, cyclobutyl, cyclopentyl, cyclohexyl and the like.

The term "$C_{3-8}$ cyclohaloalkyl" means a $C_{3-8}$ cycloalkyl as defined herein substituted by halo as defined herein.

The term "$C_{3-8}$ cyclodihaloalkyl" means a $C_{3-8}$ cycloalkyl as defined herein substituted twice by halo as defined herein where the halo atoms can be the same or different.

The term "$C_{3-8}$ cyclotrihaloalkyl" means a $C_{3-8}$ cycloalkyl as defined herein substituted thrice by halo as defined herein where the halo atoms can be the same or different.

The term "$C_2$ to $C_{10}$ dialcohol" means an alcohol containing two hydroxyl groups and 2, 3, 4, 5, 6, 7, 8, 9 or 10 carbon atoms.

The term "$C_{1-6}$ haloalkyl" means a $C_{1-6}$ alkyl as defined herein substituted once by halo as defined herein.

The term "$C_{1-6}$ dihaloalkyl" means a $C_{1-6}$ alkyl as defined herein substituted twice by halo as defined herein where the halo atoms can be the same or different.

The term "fluoro" means the chemical element fluorine.

The term "fluoromethylsulfonyl" means a $CH_2FSO_2$— radical.

The term "fluoromethylsulfoxy" means a $CH_2FSO$— radical.

The term "fluoromethylthio" means a $CH_2FS$— radical.

The term "halo" or "halogen" means fluoro, chloro, bromo or iodo.

"Haloalkyl" means an alkyl as described above wherein one or more hydrogens are replaced by halo as defined herein.

The term "halo substituted phenyl" means a phenyl as defined herein substituted by halo as defined herein.

The term "$C_{3-6}$ heterocyclic group" means a ring system radical where one or more of the ring-forming carbon atoms is replaced by a heteroatom, such as an oxygen, nitrogen, or sulfur atom, which include mono- or polycyclic (e.g., having 2 or more fused rings) ring systems as well as spiro ring systems. The ring system can contain 3, 4, 5, or 6 carbon atoms and can be aromatic or non-aromatic.

The term "methylsulfonyl" means a $CH_3SO_2$— radical.

The term "methylsulfoxy" means a $CH_3SO$— radical.

The term "methylthio" means a $CH_3S$— radical.

The term "$C_1$ to $C_{10}$ monoalcohol" means an alcohol containing one hydroxyl group and 1, 2, 3, 4, 5, 6, 7, 8, 9 or 10 carbon atoms.

The term "nitro" means a —$NO_2$ radical.

"Phenyl" means the monovalent radical $C_6H_5$ of benzene, which is the aromatic hydrocarbon $C_6H_6$.

The term "phenyl alkyl" means an alkyl as defined herein substituted by phenyl as defined herein.

The term "$C_1$ to $C_{10}$ trialcohol" means an alcohol containing three hydroxyl groups and 1, 2, 3, 4, 5, 6, 7, 8, 9 or 10 carbon atoms.

The term "$C_{1-6}$ trihaloalkyl" means a $C_{1-6}$ alkyl as defined herein substituted thrice by halo as defined herein where the halo atoms can be the same or different.

The term "$C_{1-6}$ alkylcarboxy" means a $C_{1-6}$ alkylcarbonyl wherein the carbonyl is in turn attached through an oxygen.

The term "$C_{1-6}$ alkylcarbonyl" means an $C_{1-6}$ alkyl as defined herein attached through a carbonyl.

The term "carbonyl" means a carbon attached to an oxygen by a double bond (C=O).

The term "$C_{1-6}$ haloalkylcarboxy" means a $C_{1-6}$ alkylcarboxy as defined herein substituted by halo as defined herein.

The term "$C_{3-8}$ cycloalkylcarboxy" means a $C_{3-8}$ cycloalkylcarbonyl wherein the carbonyl is in turn attached through an oxygen.

The term "$C_{3-8}$ cycloalkylcarbonyl" means a $C_{3-8}$ cycloalkyl as defined herein attached through a carbonyl.

The term "$C_{2-6}$ alkenylcarboxy" means a $C_{2-6}$ alkenylcarbonyl as defined herein wherein the carbonyl is in turn attached through an oxygen.

The term "$C_{2-6}$ alkenylcarbonyl" means a $C_{2-6}$ alkenyl as defined herein attached through a carbonyl.

The term "$C_{2-6}$ alkynylcarboxy" means a $C_{2-6}$ alkynylcarbonyl wherein the carbonyl is in turn attached through an oxygen.

The term "$C_{2-6}$ alkynylcarbonyl" means a $C_{2-6}$ alkynyl as defined herein attached through a carbonyl.

The term "$C_{1-6}$ alkoxycarboxy" means a $C_{1-6}$ alkoxycarbonyl wherein the carbonyl is in turn attached through an oxygen.

The term"$C_{1-6}$ alkoxycarbonyl" means a $C_{1-6}$ alkoxy as defined herein attached through a carbonyl.

The term "$C_{3-6}$ heterocyclic carboxy" means a $C_{3-6}$ heterocyclic carbonyl wherein the carbonyl is in turn attached through an oxygen.

The term "$C_{3-6}$ heterocyclic carbonyl" means a $C_{3-6}$ heterocyclic group as defined herein attached through a carbonyl.

The term "benzylcarboxy" means a benzylcarbonyl wherein the carbonyl is in turn attached through an oxygen.

The term "benzylcarbonyl" means a benzyl as defined herein attached through a carbonyl.

The term "phenylcarboxy" means a phenylcarbonyl wherein the carbonyl is in turn attached through an oxygen.

The term "phenylcarbonyl" means a phenyl as defined herein attached through a carbonyl.

The term "phenyl alkylcarboxy" means a phenyl alkylcarbonyl wherein the carbonyl is in turn attached through an oxygen.

The term "phenyl alkylcarbonyl" means a phenyl alkyl as defined herein attached through a carbonyl.

The term "with or without isolation" means that the compound of interest can be separated or isolated from the reaction mixture. Such separated or isolated compound can be washed, dried, purified or otherwise manipulated such that the compound can be successfully reacted in the subsequent chemical step. Alternatively, the compound of interest can be used directly in the subsequent chemical step without separating or isolating the compound from the original reaction mixture.

Throughout the specification and the appended claims, a given chemical formula or name shall encompass all stereo and optical isomers and racemates thereof, as well as mixtures in different proportions of the separate enantiomers, where such isomers and enantiomers exist, as well as pharmaceutically acceptable salts thereof and solvates thereof such as for instance hydrates. Isomers can be separated using conventional techniques, e.g., chromatography or fractional crystallization. The enantiomers can be isolated by separation of a racemic mixture, for example, by fractional crystallization, resolution or high-performance (or -pressure) liquid chromatography (HPLC). The diastereomers can be isolated by separation of isomer mixtures, for instance, by fractional crystallization, HPLC or flash chromatography. The stereoisomers also can be made by chiral synthesis from chiral starting materials under conditions which will not cause racemization or epimerization, or by derivatization, with a chiral reagent. The starting materials and conditions will be within the skill of one skilled in the art. All stereoisomers are included within the scope of the invention.

The compounds of this invention contain one or more asymmetric carbon atoms and thus occur as racemates and racemic mixtures, single enantiomers, diastereomeric mixtures and individual diastereomers. All such isomeric forms of these compounds are expressly encompassed by the present invention. Each stereogenic carbon may have the R or S configuration. Although specific compounds described herein may be depicted in a particular stereochemical configuration, such compounds having either the opposite stereochemistry at any given chiral center or mixtures thereof are envisioned as part of the invention.

The reactions described herein can be carried out in a suitable reaction vessel which is a container known to those of ordinary skill in the art that is capable of holding the reactants while allowing the reaction steps to proceed to completion. The size and type of vessel might, e.g., depend upon the size of the batch and the specific reactants selected.

In some embodiments, the present invention provides a process for preparing an ester oxazoline compound of Formula III:

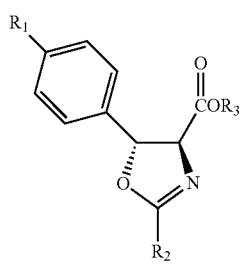

Formula III wherein:

$R_1$ is hydrogen, methylthio, methylsulfoxy, methylsulfonyl, fluoromethylthio, fluoromethylsulfoxy, fluoromethylsulfonyl, nitro, fluoro, bromo, chloro, acetyl, benzyl, phenyl, halo substituted phenyl, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{3-6}$ heterocyclic group;

$R_2$ is hydrogen, $C_{1-6}$ alkyl, $C_{1-6}$ haloalkyl, $C_{1-6}$ dihaloalkyl, $C_{1-6}$ trihaloalkyl, $CH_2Cl$, $CHCl_2$, $CCl_3$, $CH_2Br$, $CHBr_2$, $CBr_3$, $CH_2F$, $CHF_2$, $CF_3$, $C_{3-8}$ cycloalkyl, $C_{3-8}$ cyclohaloalkyl, $C_{3-8}$ cyclodihaloalkyl, $C_{3-8}$ cyclotrihaloalkyl, $C_{2-6}$ alkenyl, $C_{2-6}$ alkynyl, $C_{1-6}$ alkoxy, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, $C_{1-6}$ alkyl or $C_{1-6}$ alkoxy; $C_{1-6}$ alkylcarboxy, $C_{1-6}$ haloalkylcarboxy, $C_{3-8}$ cycloalkylcarboxy, $C_{2-6}$ alkenylcarboxy, $C_{2-6}$ alkenylcarboxy, $C_{2-6}$ alkynylcarboxy, $C_{1-6}$ alkoxycarboxy, $C_{3-6}$ heterocyclic carboxy, benzylcarboxy, phenylcarboxy, phenyl alkylcarboxy where the phenyl ring may be substituted by one or two halogens, $C_{1-6}$ alkyl or $C_{1-6}$ alkoxy or an acid addition salt thereof; and $R_3$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy.

An ester oxazoline compound of Formula III of the present invention is a useful intermediate in the formation of Florfenicol and related compounds.

In some embodiments, a process of the present invention for preparing an ester oxazoline of Formula III includes the step of:

reacting an imidate of Formula IV or an acid addition salt thereof:

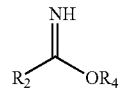

Formula IV wherein:

$R_2$ is as previously defined and $R_4$ is hydrogen, $C_{1-6}$ alkyl, $C_{1-6}$ haloalkyl, $C_{3-8}$ cycloalkyl, $C_{2-6}$ alkenyl, $C_{2-6}$ alkynyl, $C_{1-6}$ alkoxy, $C_{1-6}$ aralkyl, $C_{2-6}$ aralkenyl, or $C_{3-6}$ heterocyclic group, benzyl, phenyl or phenyl alkyl where the phenyl ring may be substituted by one or two halogens, $C_{1-6}$ alkyl or $C_{1-6}$ alkoxy or an acid addition salt thereof, with a 2-amino-3-hydroxy propanoate compound of Formula VI:

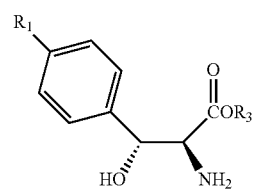

Formula VI wherein $R_1$ and $R_3$ are as previously defined, in the presence of a solvent to form an ester oxazoline of Formula III. Optionally, an acid or base may be employed to facilitate the reaction of the compound of Formula IV or its acid addition salt with the compound of Formula VI to form the ester oxazoline compound of Formula III.

Imidates of Formula IV can be prepared by methods known to those skilled in the art as described, for example, by Nakajima and LTbukata in *Science of Synthesis* (2005), 22 343-360; and by Neilson in *Chem. Amidines Imidates* (1991), 2 425-83. An imidate or its acid addition salt when $R_2$ is $CHCl_2$ and when $R_4$ is ethyl can be prepared as described, for example, by Williams et al. in *Organic Letters* (2005) Vol. 7, No 19, 4099-4102; and by UK Patent 698,543. The imidate or its acid addition salt when $R_2$ is phenyl and $R_4$ is ethyl can be prepared as described, for example, by *European J. Org Chem* (2), 452-456, 2005 and by *J. Org Chem* 55(14) 4337-4339, 1990. The contents of each of these documents are incorporated herein by reference. Other modes of preparation of an imidate of Formula IV are also known to those skilled in the art.

In particular embodiments of the invention, a compound of Formula III is a compound of Formula IIIa:

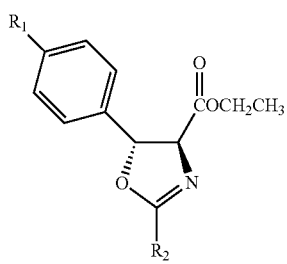

Formula IIIa

In particular embodiments of the invention, a compound of Formula III is a compound of Formula IIIb:

Formula IIIb

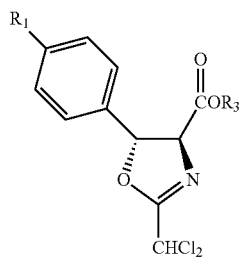

In particular embodiments of the invention, a compound of Formula III is a compound of Formula IIIc:

Formula IIIc

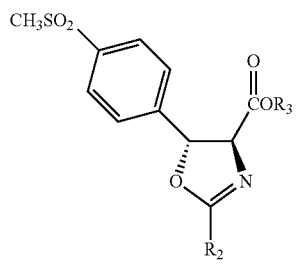

In particular embodiments of the invention, a compound of Formula III is a compound of Formula IIId:

Formula IIId

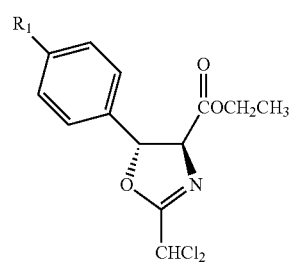

In particular embodiments of the invention, a compound of Formula III is a compound of Formula IIIe:

Formula IIIe

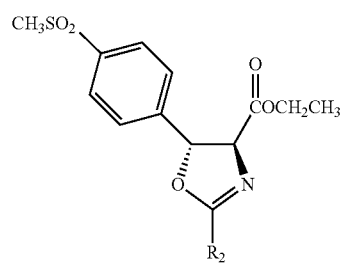

In particular embodiments of the invention, a compound of Formula III is a compound of Formula IIIf:

Formula IIIf

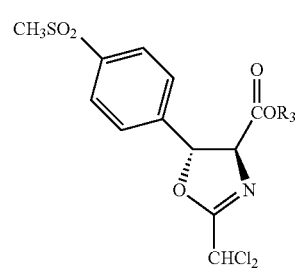

In particular embodiments of the invention, a compound of Formula III is a compound of Formula IIIg:

Formula IIIg

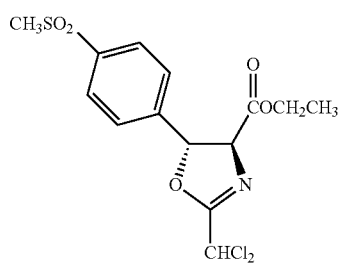

In particular embodiments of the invention, a compound of Formula III is a compound of Formula IIIh:

Formula IIIh

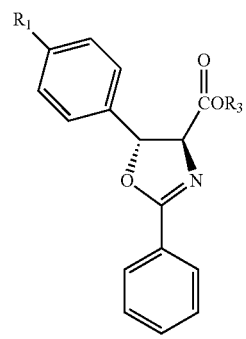

In particular embodiments of the invention, a compound of Formula III is a compound of Formula IIIi:

Formula IIIi

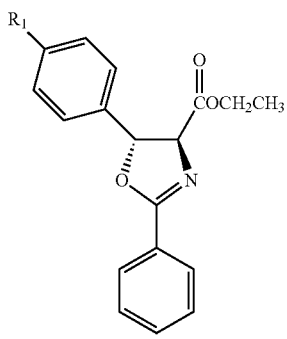

In particular embodiments of the invention, a compound of Formula III is a compound of Formula IIIj:

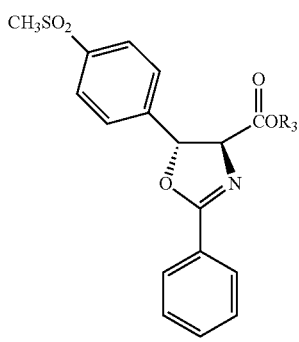

Formula IIIj

In particular embodiments of the invention, a compound of Formula III is a compound of Formula IIIk:

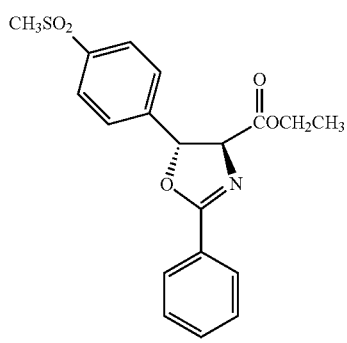

Formula IIIk

A wide range of suitable solvents can be employed when reacting an imidate of Formula IV or an acid addition salt thereof with a 2-amino-3-hydroxy propanoate compound of Formula VI to form a compound of Formula III. A non-limiting list of suitable solvents includes acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

A wide range of acids or bases can optionally be employed to facilitate the reaction of the compound of Formula IV or its acid addition salt with the compound of Formula VI to form the ester oxazoline compound of Formula III.

A non-limiting list of suitable acids includes inorganic acids, such as dilute aqueous hydrochloric acid, sulfuric acid, nitric acid, phosphoric acid and a mixture thereof, as well as organic acids, such as acetic acid, trifluoroacetic acid, methanesulfonic acid, p-toluene sulfonic acid and a mixture thereof. In some embodiments, the acid catalyst is a mixture of at least one inorganic acid and at least one organic acid. In some embodiments, the acid catalyst comprises p-toluene sulfonic acid.

A non-limiting list of suitable bases includes inorganic bases, such as LiOH, NaOH, KOH, $Li_2CO_3$, $Na_2CO_3$, $K_2CO_3$, $NH_4OH$ and a mixture thereof, as well as organic bases such as triethylamine, trimethylamine, pyridine and a mixture thereof. In some embodiments, the base is a mixture of at least one inorganic base and at least one organic base. In some embodiments, the base comprises triethylamine.

In other embodiments of the present invention, there is provided a process for preparing an oxazoline compound of Formula II:

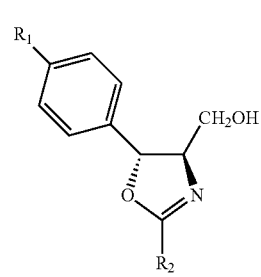

Formula II wherein $R_1$ and $R_2$ are as defined above.

An oxazoline compound of Formula II of the present invention is a useful intermediate in the formation of Florfenicol and related compounds.

In some embodiments, a process of the present invention for preparing an oxazoline of Formula II includes the steps of:

a) reducing a compound of Formula VI:

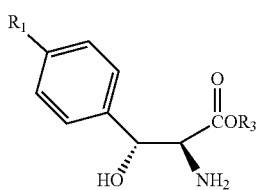

Formula VI wherein:

$R_1$ is as previously defined and $R_3$ is hydrogen, $C_{1-6}$ alkyl, $C_{3-8}$ cycloalkyl, benzyl, phenyl or phenyl alkyl where the phenyl ring may be substituted by one or two halogens, $C_{1-6}$ alkyl or $C_{1-6}$ alkoxy, (with or without isolation) in the presence of a solvent to form a compound of Formula V:

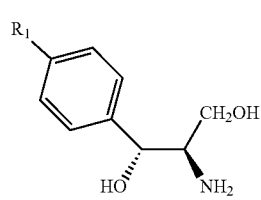

Formula V wherein $R_1$ is as previously defined, and b) reacting an imidate of Formula IV or an acid addition salt thereof:

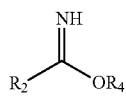
Formula IV wherein:

$R_2$ and $R_4$ are as previously defined, in a solvent with a compound of Formula V resulting from step a) to form a compound of Formula II. Optionally, an acid or base may be employed to facilitate the reaction of the compound of Formula IV or its acid addition salt with the compound of Formula V to form the ester oxazoline compound of Formula II.

Imidates useful in forming a compound of Formula II can be prepared as described above.

In particular embodiments of the invention, a compound of Formula VI is a compound of Formula VIa or an acid addition salt thereof:

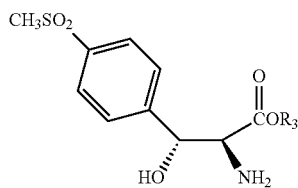
Formula VIa

In some embodiments, a compound of Formula VIa is the acid addition salt. More particularly, the acid addition salt is a HCl or $H_2SO_4$ salt.

In particular embodiments of the invention, a compound of Formula VI is a compound of Formula VIb or an acid addition salt thereof:

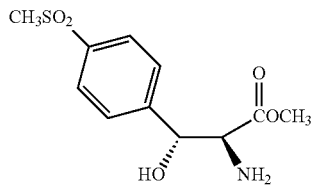
Formula VIb

In some embodiments, a compound of Formula VIb is the acid addition salt. More particularly, the acid addition salt is a HCl or $H_2SO_4$ salt.

In particular embodiments of the invention, a compound of Formula VI is a compound of Formula VIc or an acid addition salt thereof:

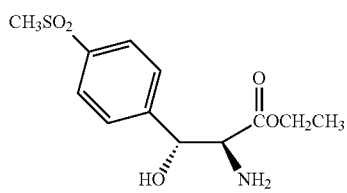
Formula VIc

In some embodiments, a compound of Formula VIc is the acid addition salt. More particularly, the acid addition salt is a HCl or $H_2SO_4$ salt.

Within the general processes described above for forming a compound of Formula II and for forming a compound of Formula III, particular embodiments of the invention are when:

$R_1$ is methylthio, methylsulfoxy or methylsulfonyl. In more particular embodiments, $R_1$ is methylsulfonyl.

$R_2$ is $CHCl_2$ or phenyl.

$R_3$ is methyl, ethyl, propyl, isopropyl, butyl, iso-butyl or pentyl. More particularly, $R_3$ is methyl or ethyl. Still more particularly, $R_3$ is ethyl.

$R_4$ is $C_{1-6}$ alkyl. More particularly, $R_4$ is methyl, ethyl, propyl, isopropyl, butyl, iso-butyl or pentyl. In more particular embodiments, $R_4$ is methyl or ethyl. In still more particular embodiments, $R_4$ is ethyl.

In particular embodiments of the invention, the acid addition salt of the compound of Formula IV or Formula VI is the HCl or $H_2SO_4$ salt.

The 2-amino-1,3-propanediol compound of Formula V can be generated in situ by reduction of a compound of Formula VI with a reducing agent in a solvent as described, for example, in U.S. Pat. No. 5,663,361, the contents of which are incorporated herein by reference. A wide range of suitable solvents can be employed in carrying out the reduction to Formula V. A non-limiting list of suitable solvents includes water, methanol, ethanol, propanol, isopropanol, butanol, pentanol, and mixtures thereof. In some embodiments, the solvent includes water, methanol, ethanol, or mixtures thereof. In particular embodiments, the solvent is an alcoholic solvent. More particularly, the solvent is methanol. The solvent for the reduction of the compound of Formula VI to the 2-amino-1,3-propanediol compound of Formula V can be replaced with an alternative solvent that facilitates the formation of the oxazoline compound of Formula II without the need to isolate the intermediate 2-amino-1,3-propanediol compound of Formula V. Such solvent replacements can be accomplished, for example, by distillation, evaporation, or extraction. In particular embodiments, the solvent for the reduction and the oxazoline formation can be the same or different.

The reduction of a compound of Formula VI to a compound of Formula V can be carried out with a wide range of reducing agents. A non-limiting list of suitable reducing agents includes $NaBH_4$, $KBH_4$, $Ca(BH_4)_2$, $LiBH_4$, and mixtures thereof. In some embodiments, the reducing agent includes $KBH_4$, $NaBH_4$, or mixtures thereof. In particular, the reducing agent is $KBH_4$.

In some embodiments of the invention, the molar ratio of the reducing agent to the compound of Formula VI is between about 1:1 and about 2:1. In particular embodiments, the molar ratio is about 1.5:1.

In some embodiments of the invention, the reduction temperature during the formation of a compound of Formula V is below about 60° C. It is also contemplated that the reduction is complete within about 6 hours.

Once a compound of Formula VI has been reduced to a compound of Formula V, a process of the invention includes the step of reacting an imidate of Formula IV or its acid addition salt with a 2-amino-1,3-propanediol compound of Formula V in a solvent such as, but not limited to, methylene chloride, chloroform, 1,2-dichloroethane, acetone, ethyl acetate, ether, tetrahydrofuran, methanol, ethanol, propanol, glycerin, water, and mixtures thereof to form an oxazoline compound of Formula II as described, for example, in Indian Patent Application 2003DE00992, *Tetrahedron*, 62(42), 9973-9980; 2006, *Helvetica Chimica Acta,* 84(5), 1093-

1111; 2001 and PCT International Application 98/06700, the contents of each of which are incorporated herein by reference.

A wide range of acids or bases can optionally be employed to facilitate the reaction of the compound of Formula IV or its acid addition salt with the compound of Formula V to form the oxazoline compound of Formula II.

A non-limiting list of suitable acids includes inorganic acids, such as dilute aqueous hydrochloric acid, sulfuric acid, nitric acid, phosphoric acid and a mixture thereof, as well as organic acids, such as acetic acid, trifluoroacetic acid, methanesulfonic acid, p-toluene sulfonic acid and a mixture thereof. In some embodiments, the acid catalyst is a mixture of at least one inorganic acid and at least one organic acid. In some embodiments, the acid catalyst comprises p-toluene sulfonic acid.

A non-limiting list of suitable bases includes inorganic bases, such as LiOH, NaOH, KOH, $Li_2CO_3$, $Na_2CO_3$, $K_2CO_3$, $NH_4OH$ and a mixture thereof, as well as organic bases such as triethylamine, trimethylamine, pyridine and a mixture thereof. In some embodiments, the base is a mixture of at least one inorganic base and at least one organic base. In some embodiments, the base comprises triethylamine.

Compounds of Formula II and Formula III can be used as intermediates for preparing Florfenicol and related compounds. Therefore, in some embodiments, a process of the invention continues by reducing a compound of Formula III in the presence of a solvent to form a compound of Formula II. As described in, for example, in U.S. Pat. No. 5,663,361 and US Patent Application 2007/0055080 A1, the contents of which are incorporated herein by reference, the ester oxazoline compound of Formula III can react with or without isolation (i.e. in situ) with a reducing agent in a solvent to form the oxazoline compound of Formula II. The solvent for the formation of the ester oxazoline compound of Formula III can be replaced with an alternative solvent that facilitates the reduction to the oxazoline compound of Formula II. Such solvent replacements can be accomplished, for example, by distillation, evaporation, or extraction. In particular embodiments, the solvent for the ester oxazoline formation and reduction are the same.

A wide range of suitable reducing agents can be employed in carrying out the reduction which produces a compound of Formula II from a compound of Formula III. A non-limiting list of suitable reducing agents includes $NaBH_4$, $KBH_4$, $Ca(BH_4)_2$, and mixtures thereof. In particular embodiments of the invention, the reducing agent includes $KBH_4$, $NaBH_4$, or mixtures thereof. In more particular embodiments, the reducing agent is $KBH_4$.

In some embodiments of the invention, the molar ratio of the reducing agent to the compound of Formula III is between about 1:1 and about 2:1. In particular embodiments, the molar ratio is about 1.5:1.

A wide range of suitable solvents can be employed in carrying out the reduction which produces a compound of Formula II. A non-limiting list of suitable solvents includes water, methanol, ethanol, propanol, isopropanol, butanol, pentanol, and mixtures thereof. In particular embodiments, the solvent includes water, methanol, ethanol, or mixtures thereof. In more particular embodiments, the solvent is methanol.

In some embodiments of the invention, the reduction temperature during the formation of a compound of Formula II is below about 60° C. It is also contemplated that the reduction is complete within about 6 hours.

Once a compound of Formula II has been prepared, it is contemplated that the process of the invention continues by fluorinating a compound of Formula II (with or without isolation) in the presence of a solvent to form a compound of Formula VII:

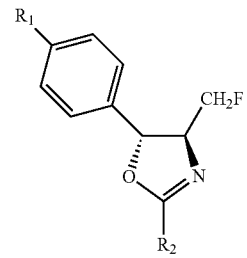

Formula VII wherein $R_1$ and $R_2$ are as previously defined.

A suitable method for the fluorination of a compound of Formula II with or without isolation (i.e. in situ) to a compound of Formula VII is described, for example, in U.S. Pat. Nos. 4,743,700; 4,876,352; 5,332,835; 5,382,673 and 5,567,844, and by Schumacher et al. in *J. Org. Chem.* 55, 5291-5294, (1990), the contents of which are incorporated herein by reference.

In particular embodiments of the invention, a compound of Formula VII is a compound of Formula VIIa:

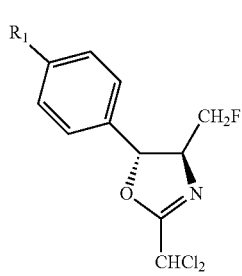

Formula VIIa

In particular embodiments of the invention, a compound of Formula VII is a compound of Formula VIIb:

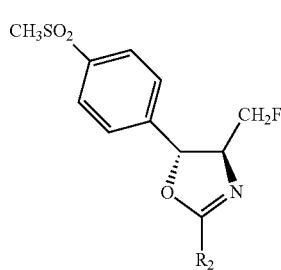

Formula VIIb

In particular embodiments of the invention, a compound of Formula VII is a compound of Formula VIIc:

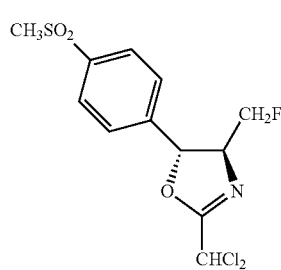

Formula VIIc

In particular embodiments of the invention, a compound of Formula VII is a compound of Formula VIId:

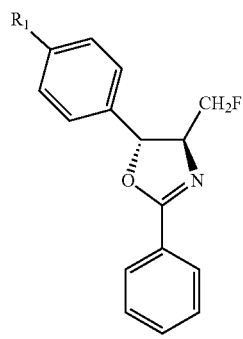

Formula VIId

In particular embodiments of the invention, a compound of Formula VII is a compound of Formula VIIe:

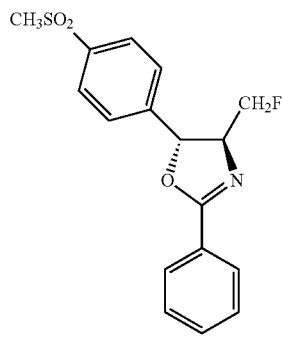

Formula VIIe

The fluorination of a compound of Formula II to a compound of Formula VII can be carried out with a wide range of fluorinating agents. A non-limiting list of suitable fluorinating agents includes sodium fluoride, potassium fluoride, cesium fluoride, tetrabutylammonium fluoride, 1,1,2,2,3,3,4,4,4-nonafluoro-1-butanesulfonyl fluoride, chloromethyl-4-fluoro-1,4-diazoniabicyclo[2.2.2]octane bis-(tetrafluoroborate), N-(2-chloro-1,1,2-trifluoroethyl)diethylamine, N-(2-chloro-1,1,2-trifluoroethyl)dimethylamine, N-(2-chloro-1,1,2-trifluoroethyl)dipropylamine, N-(2-chloro-1,1,2-trifluoroethyl)pyrrolidine, N-(2-chloro-1,1,2-trifluoroethyl)-2-methylpyrrolidine, N-(2-chloro-1,1,2-trifluoroethyl)-4-methylpiperazine, N-(2-chloro-1,1,2-trifluoroethyl)-morpholine, N-(2-chloro-1,1,2-trifluoroethyl)piperidine, 1,1,2,2-tetrafluoroethyl-N,N-dimethylamine, (Diethylamino)sulfur trifluoride, Bis-(2-methoxyethyl)aminosulfur trifluoride, N,N-diethyl-1,1,2,3,3,3-hexafluoro-1-propanamine, and mixtures thereof. Particularly, the fluorinating agent is N,N-diethyl-1,1,2,3,3,3-hexafluoro-1-propanamine (Ishikawa Reagent).

In some embodiments, the molar ratio of the fluorinating agent to a compound of Formula II is between about 1:1 and about 2:1. In particular embodiments, the molar ratio is about 1.5:1.

In some embodiments, the fluorination is carried out at a temperature of from about 80° C. to about 110° C. and at a pressure of at least about 60 psi.

A wide range of suitable solvents can be employed in carrying out the fluorination which produces a compound of Formula VII. A non-limiting list of suitable solvents includes 1,2-dichloroethane, methylene chloride, chloroform, carbon tetrachloride, a chlorinated hydrocarbon, and mixtures thereof. In particular, the solvent is methylene chloride.

It is contemplated that the process of the invention continues to form a compound of Formula XI, for example, by employing at least one of the following two methods. In a first method, a compound of Formula VII is hydrolyzed (with or without isolation) to form a compound of Formula VIII:

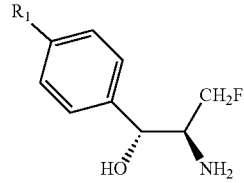

Formula VIII wherein $R_1$ is as previously defined.

The hydrolysis of a compound of Formula VII with or without isolation (i.e. in situ) to a compound of Formula VIII can be accomplished by methods described in, for example, U.S. Pat. Nos. 5,105,009; 5,567,844, and in Schumacher et al. in *J. Org. Chem.* 55, 5291-5294, (1990), the contents of which are incorporated herein by reference.

The hydrolysis of a compound of Formula VII to a compound of Formula VIII can be carried out with an acidic or basic catalyst in a solvent. A wide range of suitable acidic and basic catalysts can be employed without limitation. In some embodiments, the acidic catalyst includes HCl, $HNO_3$, $H_2SO_4$, $H_3PO_4$, acetic acid, trifluoroacetic acid, methanesulfonic acid, an organic acid of the Formula $R_4C(O)OH$ wherein $R_4$ is as defined above, or mixtures thereof. In particular embodiments, the acidic catalyst is HCl. In some embodiments, the basic catalyst includes NaOH, KOH, LiOH, $Na_2CO_3$, $K_2CO_3$, $NaHCO_3$, $KHCO_3$, $NH_4OH$, triethylamine, trimethylamine, sodium methoxide, sodium ethoxide, potassium methoxide, potassium ethoxide, or mixtures thereof. In particular embodiments, the basic catalyst includes NaOH, KOH, $NH_4OH$, or a mixture thereof.

A wide range of suitable solvents can be employed in carrying out the hydrolysis which produces a compound of Formula VIII. A non-limiting list of suitable solvents includes acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water and mixtures thereof.

In some embodiments, the solvent includes methanol, ethanol, 2-propanol, water, and mixtures thereof. In particular embodiments, the solvent is water.

In some embodiments, the hydrolysis temperature during the formation of a compound of Formula VIII is up to the reflux point of the solvent.

After formation of a compound of Formula VIII, the process of the invention can continue by acylating a compound of Formula VIII (with or without isolation) in the presence of a solvent and a base by a compound of the Formula $R_5COR_2$, wherein $R_2$ is as previously defined and $R_5$ is OH, $C_{1-6}$ alkoxy or halo, to produce a compound of Formula IX:

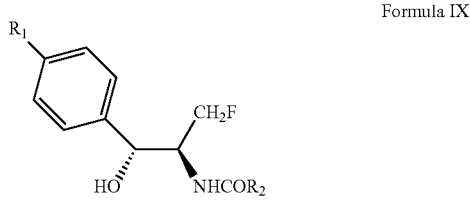

Formula IX wherein $R_1$ and $R_2$ are as previously defined.

Within the general processes described above, $R_5$ is OH, $CH_3CH_2O$, $CH_3O$, Cl or Br in particular embodiments of the invention.

The acylation of a compound of Formula VIII with or without isolation (i.e. in situ) can be accomplished, for example, by methods described in Schumacher et al. in *J. Org. Chem.* 55, 5291-5294, (1990); U.S. Pat. No. 5,105,009 and WO 2006/136919 A1, the contents of which are incorporated herein by reference.

In some embodiments of the invention, the acylating of a compound of Formula VIII to a form compound of Formula IX is carried out with an acylating agent. A wide range of acylating agents can be employed without limitation. Suitable acylating agents include dichloroacetic acid and reactive derivatives thereof. In some embodiments, the acylating agent includes methyl dichloroacetate, ethyl dichloroacetate, dichloroacetylchloride, or a mixture thereof. In particular embodiments, the acylating agent is methyl dichloroacetate.

A wide range of suitable solvents can be employed in carrying out the acylating which produces a compound of Formula IX. A non-limiting list of suitable solvents includes acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof. In some embodiments, the solvent includes methanol, ethanol, isopropanol, propanol, water, or a mixture thereof. In particular embodiments, the solvent is methanol.

In some embodiments, the acylating temperature during the formation of a compound of Formula IX is up to the boiling point of the solvent.

A wide range of suitable bases can be employed in carrying out the acylating which produces a compound of Formula IX. A non-limiting list of suitable bases includes an organic base, an inorganic base, and mixtures thereof. In some embodiments, the organic base includes triethylamine, trimethylamine, or a mixture thereof. In some embodiments, the inorganic base includes NaOH, KOH, LiOH, $Na_2CO_3$, $K_2CO_3$, $NaHCO_3$, $KHCO_3$, or a mixture thereof.

In some embodiments, the base is triethylamine.

In a second method to form a compound of Formula IX from a compound of Formula VII, a compound of Formula VII is selectively hydrolyzed (with or without isolation) to form a compound of Formula IX. Such a method is described in, for example, U.S. Pat. No. 5,382,673 and in Wu et al. in *J. Org. Chem.* 62, 2996-98 (1997), the contents of which are incorporated herein by reference.

In some embodiments of the invention, the selective hydrolysis which forms a compound of Formula IX is carried out with water and an acidic catalyst or basic catalyst in a solvent.

A wide range of suitable acidic and basic catalysts can be employed in carrying out the selective hydrolysis which produces a compound of Formula IX. Suitable acidic catalysts include, without limitation, at least one inorganic acid, at least one organic acid, and mixtures thereof. In some embodiments, the acidic catalyst includes a dilute aqueous hydrochloric acid, sulfuric acid, nitric acid, phosphoric acid, acetic acid, trifluoroacetic acid, methanesulfonic acid, p-toluene sulfonic acid, or a mixture thereof. In particular embodiments, the acidic catalyst is p-toluene sulfonic acid. Suitable basic catalysts include, without limitation, at least one inorganic base, at least one organic base, and mixtures thereof. In some embodiments, the basic catalyst includes LiOH, NaOH, KOH, $Li_2CO_3$, $Na_2CO_3$, $K_2CO_3$, $NH_4OH$ sodium methoxide, sodium ethoxide, potassium methoxide, potassium ethoxide, or a mixture thereof. In particular embodiments, the basic catalyst is $NH_4OH$.

In some embodiments of the invention, the temperature during formation of a compound of Formula IX by selective hydrolysis is less than or equal to about 100° C. In particular embodiments, the temperature is less than about 30° C.

In particular embodiments, the solvent is selected from acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof.

In some embodiments, the organic solvent comprises isopropanol, methylene chloride or a mixture thereof. In some embodiments, the mixture of an organic solvent and water comprises methylene chloride and water.

In some embodiments, about 0.5 to about 3 molar equivalents of water are used for each mole of the compound of Formula VII during the selective hydrolysis which produces a compound of Formula IX. In particular embodiments, about 1 to about 2 molar equivalents of water are used for each mole of the compound of Formula VII.

A compound of Formula IX is Florfenicol (Formula I) when $R_1$ is methyl sulfonyl and $R_2$ is $CHCl_2$. It is contemplated that a compound of Formula IX can be purified with a mixture including, but not limited to, a $C_{1-10}$ alkyl mono, di or tri alcohol and water to form a pure form of a compound of Formula IX. In some embodiments, the purification is carried out in a mixture including methanol, ethanol, propanol, isopropanol, butanol, sec-butanol, t-butanol, pentanol, ethylene glycol, propylene glycol, butylene glycol, glycerin, water, or mixtures thereof. In particular embodiments, the purification is carried out in a mixture including methanol, ethanol, propanol, isopropanol, butanol, sec-butanol, t-butanol, pentanol, water, or mixtures thereof. In more particular embodiments, the purification is carried out in a mixture comprising isopropanol, water, or mixtures thereof. Methods for purifying the compound of Formula IX in a mixture of an alcohol and water suitable for use in the present invention are described, for example, in Schumacher et al. in *J. Org. Chem.* 55, 5291-5294, (1990), and in US Patent Applications 2007/00550661 A1, 2007/0055067 A1 and 2007/0055080 A1.

In some embodiments of the invention, the ratio of isopropanol to water during purification is between about 1:5 and about 5:1. In particular embodiments, the ratio of isopropanol to water is about 1:1.

In some embodiments, the dissolution temperature for purification is the reflux point of about 1:1 isopropanol and water.

In some embodiments, the purification reaction is cooled to about 10-30° C. to crystallize the purified form of the compound of Formula IX. In particular embodiments, the purification reaction is cooled to about 20-25° C.

Suitable variations of the embodiments of the invention disclosed herein will be apparent to those skilled in the art. Therefore, it should be understood that this disclosure and the accompanying claims are intended to cover all variations, modifications and equivalents of the embodiments of the invention disclosed herein.

EXAMPLES

The following examples represent processes and compounds of the present invention. While the present invention has been described with specificity in accordance with certain embodiments of the present invention, the following examples further serve only to exemplify and illustrate the present invention and are not intended to limit or restrict the effective scope of the present invention.

Example 1

Preparation of (4S-trans)-4,5-Dihydro-5-[4-(methylsulfonyl)phenyl]-2-phenyl-4-oxazolecarboxylic acid ethyl ester (Compound IIIk)

(2S,3R)-Ethyl-2-amino-3-[4-(methylsulfonyl)phenyl]-3-hydroxy-propanoate (Compound VIc) (10 g, 0.0348 moles) is reacted at about 0° C. in a reaction vessel with benzenecarboximidic acid ethyl ester hydrochloride (Compound IV hydrochloride salt wherein $R_2$ is phenyl and $R_4$ is ethyl) (about 7.1 g, 0.03828 moles) in 1,2-dichloromethane (about 650 mL) containing triethylamine (3.9 g, 0.03828 moles). Thereafter, water is added (about 500 mL). Next, the organic layer is separated and washed with dilute hydrochloric acid (about 1 N) and dilute sodium bicarbonate (about 1N). The washed organic layer is dried over anhydrous sodium sulfate. The dried organic layer is heated to evaporate the 1,2-dichloromethane to yield (4S-trans)-4,5-dihydro-5-[4-(methylsulfonyl)phenyl]-2-phenyl-4-oxazolecarboxylic acid ethyl ester (Compound IIIk).

Example 2

Preparation of (4R,5R)-4,5-Dihydro-5-[4-(methylsulfonyl)phenyl]-2-phenyl-4-oxazolemethanol (Compound II wherein $R_1$ is methylsulfonyl, $R_2$ is phenyl and $R_3$ is ethyl)

(4S-trans)-4,5-Dihydro-5-[4-(methylsulfonyl)phenyl]-2-phenyl-4-oxazolecarboxylic acid ethyl ester (Compound IIIk) (about 5 g, 0.0134 moles) in methanol (about 50 mL) is reacted in a reaction vessel with potassium borohydride (about 1.1 g, 0.0201 moles) over about 6 hours while maintaining the temperature below about 60° C. The reaction is cooled to ambient room temperature and about 1N HCl (about 10 mL) and water (about 50 mL) are added. The resulting solids are filtered, washed with water, then dried to yield (4R,5R)-4,5-Dihydro-5-[4-(methylsulfonyl)phenyl]-2-phenyl-4-oxazolemethanol (Compound II wherein $R_1$ is methylsulfonyl, $R_2$ is phenyl and $R_3$ is ethyl).

Example 3

Preparation of (4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl)

(2S,3R)-Ethyl-2-amino-3-[4-(methylsulfonyl)phenyl]-3-hydroxy-propanoate (Compound VIc) (10 g, 0.0348 moles) is reacted at about ambient room temperature in a reaction vessel with benzenecarboximidic acid ethyl ester hydrochloride (Compound IV wherein $R_2$ is phenyl and $R_4$ is ethyl) (about 7.37 g, 0.03828 moles) in 1,2-dichloromethane (about 650 mL) containing triethylamine (about 3.9 g, 0.03828 moles). Thereafter, water (about 500 mL) is added. Next, the organic layer is separated. Thereafter, the organic layer is heated to evaporate the 1,2-dichloromethane, and methanol is added (about 50 mL) to yield (4S-trans)-4,5-Dihydro-5-[4-(methylsulfonyl)phenyl]-2-phenyl-4-oxazolecarboxylic acid ethyl ester (Compound IIIk) which is not isolated. The unisolated compound is reacted with potassium borohydride (about 2.8 g, 0.0522 moles) over about 6 hours while maintaining the temperature below about 60° C. The reaction is cooled to ambient room temperature and about 1N HCl (about 10 ml) and water (about 500 ml) are added. The resulting solids are filtered, washed with water, then dried to yield (4R,5R)-4,5-dihydro-5-[4-(methylsulfonyl)phenyl]-2-phenyl-4-oxazolemethanol (Compound II wherein $R_1$ is methylsulfonyl, $R_2$ is phenyl and $R_3$ is ethyl).

Example 4

Preparation of (4S-trans)-4,5-Dihydro-5-[4-(methylsulfonyl)phenyl]-2-dichloromethyl-4-oxazolecarboxylic acid ethyl ester (Compound IIIg)

(2S,3R)-Ethyl-2-amino-3-[4-(methylsulfonyl)phenyl]-3-hydroxy-propanoate (Compound VIc) (10 g, 0.0348 moles) is reacted in a reaction vessel with 2,2-dichloro-ethanimidic acid ethyl ester (Compound IV wherein $R_2$ is dichloromethyl and $R_4$ is ethyl) (about 6.0 g, 0.03828 moles) in 1,2-dichloromethane (about 400 mL) containing triethylamine (about 0.4 g, 0.0038 moles). Next, water (about 300 mL) is added. Thereafter, the organic layer is separated and washed with dilute hydrochloric acid (about 1 N) and dilute sodium bicarbonate (about 1 N). The washed organic layer is dried over anhydrous sodium sulfate. Next, the 1,2-dichloromethane is evaporated to yield (4S-trans)-4,5-dihydro-5-[4-(methylsulfonyl)phenyl]-2-dichloromethyl-4-oxazolecarboxylic acid ethyl ester (Compound IIIg).

Example 5

Preparation of (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl)

(4S-trans)-4,5-Dihydro-5-[4-(methylsulfonyl)phenyl]-2-phenyl-4-oxazolecarboxylic acid ethyl ester (Compound IIIk) (about 5 g, 0.0131 moles) in methanol (about 50 mL) is reacted in a reaction vessel with potassium borohydride (about 1.1 g, 0.0197 moles) over about 6 hours while maintaining the temperature below about 60° C. The reaction is cooled to ambient room temperature and about 1N HCl and water (about 50 mL) are added. The resulting solids are filtered, washed with water, then dried to yield (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl).

Example 6

Preparation of (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl)

(2S,3R)-Ethyl-2-amino-3-[4-(methylsulfonyl)phenyl]-3-hydroxy-propanoate (Compound VIc) (10 g, 0.0348 moles) is reacted at about 0° C. in a reaction vessel with 2,2-dichloroethanimidic acid ethyl ester (Compound IV wherein $R_2$ is dichloromethyl and $R_4$ is ethyl) (about 6.0 g, 0.03828 moles) in 1,2-dichloromethane (about 500 mL) containing triethylamine (about 0.4 g, 0.0038 moles). The organic layer is heated to evaporate the 1,2-dichloromethane, and methanol is added (about 50 mL) to yield (4S-trans)-4,5-Dihydro-5-[4-(methylsulfonyl)phenyl]-2-dichloromethyl-4-oxazolecarboxylic acid ethyl ester (Compound IIIg) which is not isolated. The unisolated compound is reacted with potassium borohydride (about 2.8 g, 0.0522 moles) over about 6 hours while maintaining the temperature below about 60° C. The reaction is cooled to ambient room temperature, about 1N HCl and water (about 450 mL) are added. The resulting solids are filtered, washed with water, then dried to yield (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl).

Example 7

Preparation of (4S,5R)-4-(Fluoromethyl)-4,5-dihydro-5-[4-(methylsulfonyl)phenyl]-2-phenyl-4-oxazole (Compound VIIe)

(4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl) (about 25 g, 0.0754 moles) in 1,2-dichloromethane (about 175 mL) is reacted in a reaction vessel with N,N-diethyl-1,1,2,3,3,3-hexafluoro-1-propanamine (about 25.2 g, 0.1131 moles) at about 95 to about 105° C. for about 4 hours. Thereafter, the solution is cooled to about 20° C. to about 25° C. The cooled solution is quenched with water (about 675 mL) containing about 25% aqueous sodium hydroxide. Next, the organic layer is separated. Thereafter, the organic layer is heated to evaporate the 1,2-dichloromethane, and isopropanol (about 75 mL) is added. The resulting solids are filtered, first washed with isopropanol (about 10 mL), then washed with water (about 10 mL), then dried to yield (4S,5R)-4-(Fluoromethyl)-4,5-dihydro-5-[4-(methylsulfonyl)phenyl]-2-phenyl-4-oxazole (Compound VIIe).

Example 8

Preparation of Florfenicol (Formula I)

(4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl) (about 5 g, 0.0147 moles) in 1,2-dichloromethane containing N,N-diethyl-1,1,2,3,3,3-hexafluoro-1-propanamine (about 4.9 g, 0.0221 moles) is reacted in a reaction vessel at about 95° C. to about 100° C. to produce (4S,5R)-2-(dichloromethyl)-4-(fluoromethyl)-4,5-dihydro-5-[4-(methylsulfonyl)phenyl]-oxazole (Compound VIIc) in situ. Compound VIIc is cooled to below about 25° C., then water (about 0.4 g, 0.0222 moles) and ammonium hydroxide (about 0.0237 moles) are added. The resulting solids are filtered, washed with about 10 mL of 1:1 isopropanol/water, then dried to yield Florfenicol (Formula I).

Example 9

Preparation of Florfenicol (Formula I)

(4S,5R)-4-(Fluoromethyl)-4,5-dihydro-5-[4-(methylsulfonyl)phenyl]-2-phenyl-4-oxazole (Compound VIIe) (about 50.0 g, 0.1500 moles) hydrolyses in water (about 300 mL) containing about 20% hydrochloric acid at about 90° C. to about 100° C. over about 1 hour. The pH is adjusted to greater than about 12 by adding sodium hydroxide. Extraction with 1,2-dichloromethane (about 500 mL) yields (1R,2S)-1-[4-(methylsulfonyl)phenyl]-2-amino-3-fluoro-1-propanol (Compound VIII wherein $R_1$ is methylsulfonyl) in solution. Thereafter, the 1,2-dichloromethane is distilled. Next, methanol is added (about 100 mL). Thereafter, the solution is agitated while adding methyl dichloroacetate (about 64.3 g, 0.4500 moles) and triethylamine (about 15.9 g, 0.1575 moles) for about 12 to about 16 hours at about 20° C. to about 25° C. After agitation, water (about 175 mL) and toluene (about 100 mL) are added to precipitate the product. The precipitated product is filtered, washed with water (about 100 mL) and toluene (about 175 mL), then dried to yield Florfenicol (Formula I).

Example 10

Purification of Florfenicol (Formula I)

Crude Florfenicol (Formula I) (about 25 g, 0.0700 moles) is dissolved in water (about 60 mL) and isopropanol (about 60 mL) at reflux. Next, charcoal (about 0.5 g) is added. Thereafter, the charcoal is removed by filtration. The filtered solution is cooled to about 20° C. to about 25° C. The resulting solids are filtered, washed with about 1:1 water/isopropanol (about 20 mL), then dried to yield pure Florfenicol (Formula I).

Example 11

Preparation of (1R,2R)-2-amino-1-[4-(methylsulfonyl)phenyl]-1,3-propanediol (Compound V wherein $R_1$ is methylsulfonyl)

(2S,3R)-Ethyl-2-amino-3-[4-(methylsulfonyl)phenyl]-3-hydroxy-propanoate (Compound VIc) (10 g, 0.0348 moles) in methanol (about 100 mL) is reacted in a reaction vessel with potassium borohydride (about 2.8 g, 0.0522 moles) over about 6 hours while maintaining the temperature below about 60° C. The reaction is cooled to ambient room temperature and about 1N HCl and water (about 75 mL) are added. Thereafter, the solution is heated to evaporate the methanol. Next, sodium hydroxide is added (about 25%), the resulting solids are filtered and washed with water, then dried to yield (1R, 2R)-2-amino-1-[4-(methylsulfonyl)phenyl]-1,3-propanediol (Compound V wherein $R_1$ is methylsulfonyl).

Example 12

Preparation of (4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl)

(2S,3R)-Ethyl-2-amino-3-[4-(methylsulfonyl)phenyl]-3-hydroxy-propanoate (Compound VIc) (10 g, 0.0348 moles) in methanol (about 100 mL) is reacted in a reaction vessel with potassium borohydride (about 2.8 g, 0.0522 moles) over about 6 hours while maintaining the temperature below about 60° C. The reaction is cooled to ambient room temperature and about 1N HCl and water (about 15 mL) are added. Thereafter, the mixture is neutralized with sodium hydroxide (about 25%) to generate (1R,2R)-2-amino-1-[4-(methylsulfonyl)phenyl]-1,3-propanediol (Compound V wherein $R_1$ is methylsulfonyl) in situ. Next, the methanol is evaporated, followed by the addition of 1,2-dichloroethane (about 250 mL). Next, benzenecarboximidic acid ethyl ester (Compound IV wherein $R_2$ is phenyl and $R_4$ is ethyl) (about 7.8 g, 0.0522 moles) is added with is heated to about 85° C. for about 6 hours. The reaction is then cooled, to below about 25° C. After cooling, glycerin is added (about 50 mL). Next, the 1,2-dichloroethane is distilled by heating to about 85° C., followed by continued heating to about 105° C. to about 110° C. for about 10 hours, then followed by cooling to below about 25° C. Thereafter, water is added (about 100 mL). The resulting solids are filtered, washed with about 1 to 1 water/isopropanol, then dried to yield (4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl).

Example 13

Preparation of (4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl)

(1R,2R)-2-amino-1-[4-(methylsulfonyl)phenyl]-1,3-propanediol (Compound V wherein $R_1$ is methylsulfonyl) (about 10 g, 0.04077) is reacted at about 0° C. in a reaction vessel with benzenecarboximidic acid ethyl ester hydrochloride (Compound IV hydrochloride wherein $R_2$ is phenyl and $R_4$ is ethyl) (about 8.3 g, 0.0448 moles) in 1,2-dichloroethane (about 650 mL) containing triethylamine (about 4.1 g, 0.04077 moles). Next, water (about 500 mL) is added. The resulting solids are filtered, then dried to yield (4R,5R)-4,5-Dihydro-5-[4-(methylsulfonyl)phenyl]-2-phenyl-4-oxazolemethanol (Compound II wherein $R_1$ is methylsulfonyl and $R_2$ is phenyl).

Example 14

Preparation of (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl)

(2S,3R)-Ethyl-2-amino-3-[4-(methylsulfonyl)phenyl]-3-hydroxy-propanoate (Compound VIc) (10 g, 0.0348 moles) in methanol (about 100 mL) is reacted in a reaction vessel with potassium borohydride (about 1.1 g, 0.0207 moles) over about 6 hours while maintaining the temperature below about 60° C. The reaction is cooled to ambient room temperature and about 1N HCl and water (about 25 ml) are added, followed by neutralization with sodium hydroxide (about 25%) to generate (1R,2R)-2-amino-1-[4-(methylsulfonyl)phenyl]-1,3-propanediol (Compound V wherein $R_1$ is methylsulfonyl) in situ. Next, the methanol is evaporated, followed by the addition of 1,2-dichloroethane (about 200 mL). Next, 2,2-dichloro-ethanimidic acid ethyl ester (Compound IV wherein $R_2$ is dichloromethyl and $R_4$ is ethyl) is added (about 10.9 g, 0.0696 moles) with heating up to about 85° C. for about 6 hours. The reaction is then cooled to below about 25° C. After cooling, glycerin is added (about 50 mL). Next, the 1,2-dichloroethane is distilled by heating to about 85° C., followed by continued heating to about 105° C. to about 110° C. for about 10 hours, then followed by cooling to below about 25° C. Thereafter, water is added (about 100 mL). The resulting solids are filtered and washed with water (about 10 mL) and isopropanol (about 10 mL) to yield (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl).

Example 15

Preparation of Preparation of (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl)

(1R,2R)-2-amino-1-[4-(methylsulfonyl)phenyl]-1,3-propanediol (Compound V wherein $R_1$ is methylsulfonyl) (about 10 g, 0.04077 moles) is reacted at about 0° C. in a reaction vessel with 2,2-dichloro-ethanimidic acid ethyl ester hydrochloride (Compound IV hydrochloride wherein $R_2$ is dichloromethyl and $R_4$ is ethyl) (about 8.6 g, 0.0448 moles) in 1,2-dichloromethane (about 250 mL) containing triethylamine (about 4.1 g, 0.04077 moles). Next, water (about 125 mL) is added. The resulting solids are filtered, then dried to yield (4R,5R)-2-(Dichloromethyl)-4,5-dihydro-5-[4-(methylsulfonyl)phenyl]-4-oxazolemethanol (Compound II wherein $R_1$ is methylsulfonyl and $R_2$ is dichloromethyl).

What is claimed is:
1. A process for preparing florfenicol comprising:
a) reacting

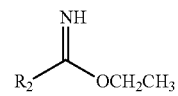

or its acid additional salt, wherein $R_2$ is $CHCl_2$ or phenyl, with

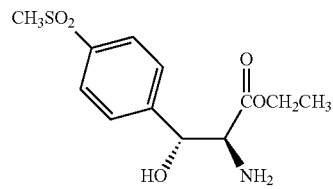

in the presence of a solvent to form

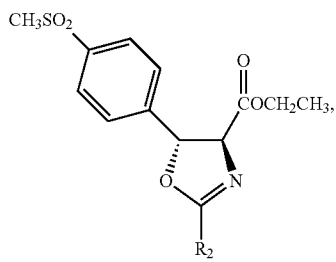

b) reducing the product resulting from step a) (with or without isolation) in the presence of a solvent to form

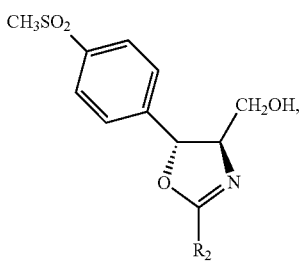

c) fluorinating the product resulting from step b) (with or without isolation) in the presence of a solvent to form

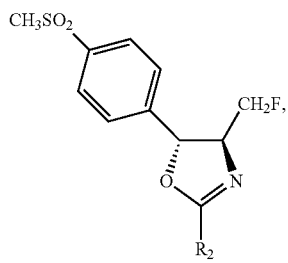

d) hydrolyzing the product resulting from step c) (with or without isolation) to form

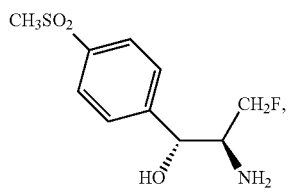

e) acylating the product resulting from step d) (with or without isolation) in the presence of a solvent and a base by a compound of the Formula $CHCl_2COOCH_3$ to form

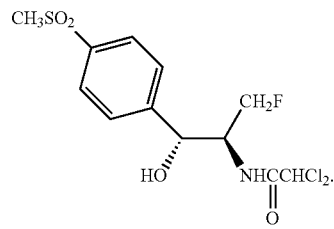

2. The process of claim 1, wherein $R_2$ is phenyl.

3. A process for preparing florfenicol comprising:

a) reacting

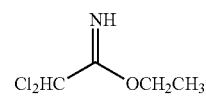

or its acid additional salt, with

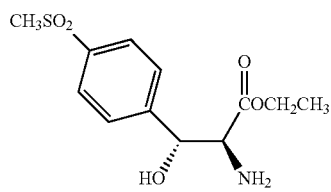

in the presence of a solvent to form

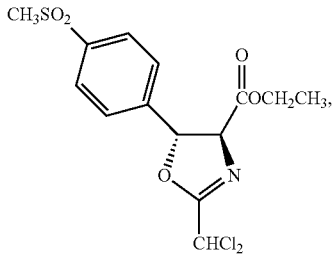

b) reducing the product resulting from step a) (with or without isolation) in the presence of a solvent to form

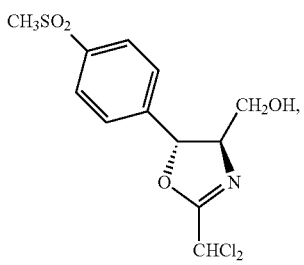

c) fluorinating the product resulting from step b) (with or without isolation) in the presence of a solvent to form

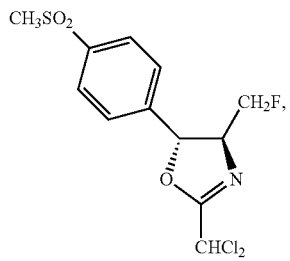

d) selectively hydrolyzing the product resulting from step c) (with or without isolation) to form

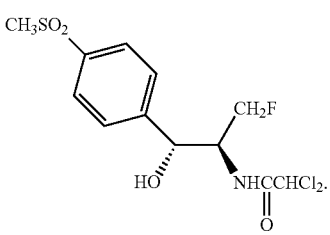

4. A process for preparing florfenicol comprising:

a) reducing

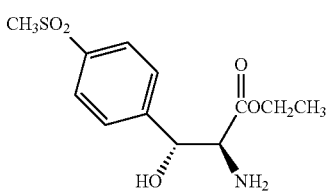

(with or without isolation) in the presence of a solvent to form

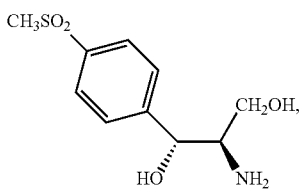

b) reacting

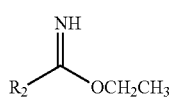

or its acid additional salt, wherein $R_2$ is $CHCl_2$ or phenyl, with the product resulting from step a) to form

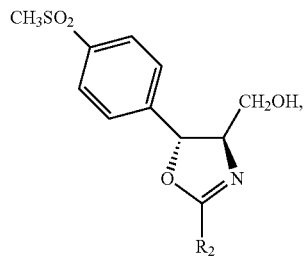

c) fluorinating the product resulting from step b) (with or without isolation) in the presence of a solvent to form

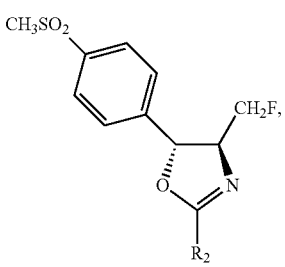

d) hydrolyzing the product resulting from step c) (with or without isolation) to form

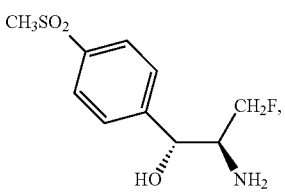

e) acylating the product resulting from step d) (with or without isolation) in the presence of a solvent and a base by a compound of the Formula $CHCl_2COOCH_3$ to form

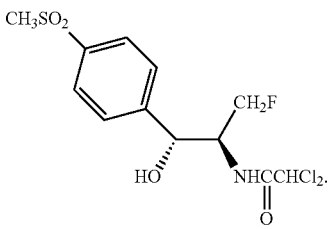

5. The process of claim 4, wherein $R_2$ is phenyl.

6. A process for preparing florfenicol comprising:

a) reducing

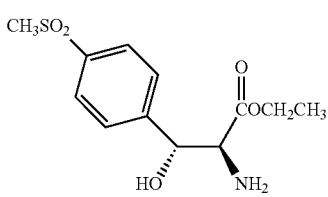

(with or without isolation) in the presence of a solvent to form
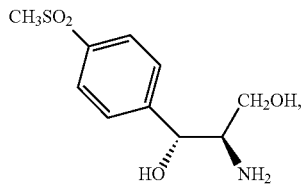
b) reacting
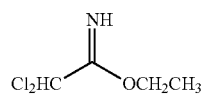
or its acid additional salt, with the product resulting from step a) to form
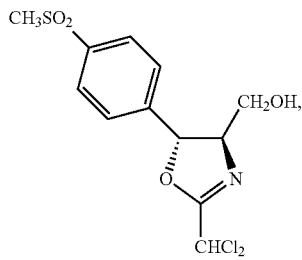
c) fluorinating the product resulting from step b) (with or without isolation) in the presence of a solvent to form
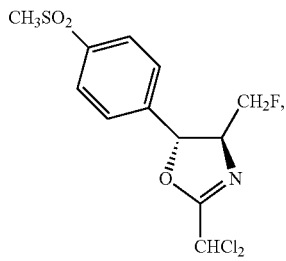
d) selectively hydrolyzing the product resulting from step c) (with or without isolation) to form
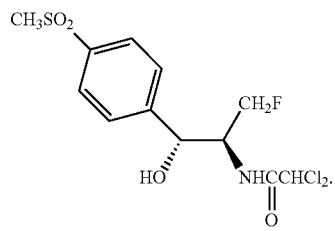
* * * * *